(12) United States Patent
Gannon et al.

(10) Patent No.: US 9,693,689 B2
(45) Date of Patent: Jul. 4, 2017

(54) BODY TEMPERATURE LOGGING PATCH

(71) Applicant: Blue Spark Technologies, Inc., Westlake, OH (US)

(72) Inventors: John Gannon, Shaker Heights, OH (US); Matt Ream, Naperville, IL (US); Gary R. Tucholski, North Royalton, OH (US)

(73) Assignee: BLUE SPARK TECHNOLOGIES, INC., Westlake, OH (US)

( * ) Notice: Subject to any disclaimer, the term of this patent is extended or adjusted under 35 U.S.C. 154(b) by 163 days.

(21) Appl. No.: 14/587,626

(22) Filed: Dec. 31, 2014

(65) Prior Publication Data

US 2016/0183794 A1  Jun. 30, 2016

(51) Int. Cl.
*A61B 5/00* (2006.01)
*A61B 5/01* (2006.01)

(52) U.S. Cl.
CPC .............. *A61B 5/0008* (2013.01); *A61B 5/01* (2013.01); *A61B 5/6833* (2013.01); *A61B 5/0024* (2013.01); *A61B 5/6898* (2013.01); *A61B 5/743* (2013.01); *A61B 2562/166* (2013.01)

(58) Field of Classification Search
CPC ......... A61B 5/01; A61B 5/015; G01K 13/002
USPC ....................................................... 600/549
See application file for complete search history.

(56) References Cited

U.S. PATENT DOCUMENTS

| | | | |
|---|---|---|---|
| 629,325 A | 7/1899 | Ashley | |
| 629,372 A | 7/1899 | Kennedy | |
| 2,154,312 A | 4/1939 | Maccallum | |
| 2,480,531 A | 8/1949 | Wilke | |
| 2,637,757 A | 5/1953 | Wilke | |
| 2,688,649 A | 9/1954 | Bjorksten | |
| 2,903,498 A | 9/1959 | Sindel et al. | |
| 2,905,738 A | 9/1959 | Di Pasquale et al. | |
| 3,006,980 A | 10/1961 | Story | |

(Continued)

FOREIGN PATENT DOCUMENTS

| | | |
|---|---|---|
| DE | 19943961 A1 | 6/2000 |
| EP | 0678927 A1 | 10/1995 |

(Continued)

OTHER PUBLICATIONS

Acheson Colloids Company, "Sales Information Bulletin," Port Huron, MI, last accessed Nov. 24, 2009.

(Continued)

*Primary Examiner* — Daniel Cerioni

(57) ABSTRACT

An actively-powered temperature data logger patch with wireless data communication includes a sealed, flexible battery comprising a printed electrochemical cell with an anode and a cathode, and a flexible circuit including a microprocessor, a temperature sensor configured to sense a temperature of a target subject, a wireless communication transmitter and an antenna. In one example, the temperature sensor is located at a first end of the patch, and the antenna is located at an opposite, second end of the patch. The patch is configured to conform to a curved surface of the target subject and includes an adhesive configured to be removably applied to skin of the patient. An external computing device is capable of receiving communication from the wireless communication transmitter of the patch via an electromagnetic field.

6 Claims, 7 Drawing Sheets

(56) References Cited

U.S. PATENT DOCUMENTS

| | | |
|---|---|---|
| 3,230,115 A | 1/1966 | Tamminen |
| 3,253,588 A | 5/1966 | Vuilleumier et al. |
| 3,375,136 A | 3/1968 | Biggar |
| 3,655,449 A | 4/1972 | Yamamoto et al. |
| 3,770,504 A | 11/1973 | Bergum |
| 3,799,808 A | 3/1974 | Hancock |
| 3,847,669 A | 11/1974 | Paterniti |
| 3,901,732 A | 8/1975 | Kalnoki Kis et al. |
| 3,928,077 A | 12/1975 | Sperandio et al. |
| 3,943,918 A | 3/1976 | Lewis |
| 3,954,506 A | 5/1976 | Sullivan |
| 3,967,292 A | 6/1976 | Delahunt |
| 3,980,497 A | 9/1976 | Gillman et al. |
| 3,988,168 A | 10/1976 | Bruneau |
| 3,993,508 A | 11/1976 | Erlichman |
| 4,001,467 A | 1/1977 | Sullivan |
| 4,006,036 A | 2/1977 | Charkoudian |
| 4,007,472 A | 2/1977 | Land |
| 4,028,479 A | 6/1977 | Fanciullo et al. |
| 4,042,760 A | 8/1977 | Land |
| 4,047,289 A | 9/1977 | Wolff |
| 4,060,669 A | 11/1977 | Fanciullo |
| 4,070,528 A | 1/1978 | Bergum et al. |
| 4,080,728 A | 3/1978 | Buckler |
| 4,086,399 A | 4/1978 | Hyland et al. |
| 4,086,400 A | 4/1978 | Hyland et al. |
| 4,098,965 A | 7/1978 | Kinsman |
| 4,105,815 A | 8/1978 | Buckler |
| 4,105,831 A | 8/1978 | Plasse |
| 4,112,205 A | 9/1978 | Charkoudian et al. |
| 4,118,860 A | 10/1978 | Buckler et al. |
| 4,119,770 A | 10/1978 | Land |
| 4,124,742 A | 11/1978 | Land et al. |
| 4,125,684 A | 11/1978 | Land |
| 4,125,685 A | 11/1978 | Bloom et al. |
| 4,125,686 A | 11/1978 | Kinsman |
| 4,136,236 A | 1/1979 | Ruetschi |
| 4,137,627 A | 2/1979 | Kinsman |
| 4,145,485 A | 3/1979 | Kinsman |
| 4,150,200 A | 4/1979 | Sullivan |
| 4,152,825 A | 5/1979 | Bruneau |
| 4,172,184 A | 10/1979 | Bloom et al. |
| 4,172,319 A | 10/1979 | Bloom et al. |
| 4,175,052 A | 11/1979 | Norteman, Jr. |
| 4,177,330 A | 12/1979 | Gordon et al. |
| 4,177,552 A | 12/1979 | Gordon et al. |
| 4,181,778 A | 1/1980 | Land |
| 4,185,144 A | 1/1980 | Ames et al. |
| 4,194,061 A | 3/1980 | Land et al. |
| 4,195,121 A | 3/1980 | Peterson |
| 4,204,036 A | 5/1980 | Cohen et al. |
| 4,232,099 A | 11/1980 | Sullivan |
| 4,242,424 A | 12/1980 | Buckler et al. |
| 4,254,191 A | 3/1981 | Kniazzeh |
| 4,256,813 A | 3/1981 | Kniazzeh |
| 4,287,274 A | 9/1981 | Ibbotson et al. |
| 4,345,954 A | 8/1982 | Panchu |
| 4,361,633 A | 11/1982 | Nel et al. |
| 4,389,470 A | 6/1983 | Plasse |
| 4,400,452 A | 8/1983 | Bruder |
| 4,427,748 A | 1/1984 | Land |
| 4,429,026 A | 1/1984 | Bruder |
| 4,455,358 A | 6/1984 | Graham et al. |
| 4,466,470 A | 8/1984 | Bruder |
| 4,477,544 A | 10/1984 | Bruder |
| 4,502,903 A | 3/1985 | Bruder |
| 4,505,996 A | 3/1985 | Simonton |
| 4,525,439 A | 6/1985 | Simonton |
| 4,532,193 A | 7/1985 | Kniazzeh et al. |
| 4,539,275 A | 9/1985 | Plasse |
| 4,554,226 A | 11/1985 | Simonton |
| 4,604,334 A | 8/1986 | Tarascon |
| 4,608,279 A | 8/1986 | Schumm, Jr. |
| 4,609,597 A | 9/1986 | Plasse |
| 4,621,035 A | 11/1986 | Bruder |
| 4,623,598 A | 11/1986 | Waki et al. |
| 4,664,993 A | 5/1987 | Sturgis et al. |
| 4,747,413 A | 5/1988 | Bloch |
| 4,756,717 A | 7/1988 | Sturgis et al. |
| 4,889,777 A | 12/1989 | Akuto |
| 4,916,035 A | 4/1990 | Yamashita et al. |
| 4,977,046 A | 12/1990 | Bleszinski, Jr. et al. |
| 4,987,579 A | 1/1991 | Yoshinaka et al. |
| 4,997,732 A | 3/1991 | Austin et al. |
| 5,035,965 A | 7/1991 | Sangyoji et al. |
| 5,055,968 A | 10/1991 | Nishi et al. |
| 5,110,696 A | 5/1992 | Shokoohi et al. |
| 5,116,701 A | 5/1992 | Kalisz |
| 5,120,785 A | 6/1992 | Walker et al. |
| 5,217,828 A | 6/1993 | Sangyoji et al. |
| 5,259,891 A | 11/1993 | Matsuyama et al. |
| 5,326,652 A | 7/1994 | Lake |
| 5,330,860 A | 7/1994 | Grot et al. |
| 5,338,625 A | 8/1994 | Bates et al. |
| 5,350,645 A | 9/1994 | Lake et al. |
| 5,401,590 A | 3/1995 | Chalilpoyil et al. |
| 5,415,888 A | 5/1995 | Banerjee et al. |
| 5,424,151 A | 6/1995 | Koksbang et al. |
| 5,445,856 A | 8/1995 | Chaloner-Gill |
| 5,455,127 A | 10/1995 | Olsen et al. |
| 5,470,357 A | 11/1995 | Schmutz et al. |
| 5,514,492 A | 5/1996 | Marincic et al. |
| 5,547,911 A | 8/1996 | Grot |
| 5,565,143 A | 10/1996 | Chan |
| 5,578,390 A | 11/1996 | Hughen |
| 5,587,254 A | 12/1996 | Kojima et al. |
| 5,620,580 A | 4/1997 | Okabe et al. |
| 5,622,652 A | 4/1997 | Kucherovsky et al. |
| 5,624,468 A | 4/1997 | Lake |
| 5,634,468 A | 6/1997 | Platt et al. |
| 5,637,418 A | 6/1997 | Brown et al. |
| 5,652,043 A | 7/1997 | Nitzan |
| 5,658,684 A | 8/1997 | Lake |
| 5,728,181 A | 3/1998 | Jung et al. |
| 5,735,912 A | 4/1998 | Lake |
| 5,735,914 A | 4/1998 | Lake |
| 5,747,190 A | 5/1998 | Lake |
| 5,747,191 A | 5/1998 | Lake |
| 5,759,215 A | 6/1998 | Masuda |
| 5,779,839 A | 7/1998 | Tuttle et al. |
| 5,811,204 A | 9/1998 | Nitzan |
| 5,862,803 A | 1/1999 | Besson et al. |
| 5,865,859 A | 2/1999 | Lake |
| 5,897,522 A | 4/1999 | Nitzan |
| 5,906,661 A | 5/1999 | Lake |
| 5,930,023 A | 7/1999 | Mitchell, Jr. et al. |
| 5,938,619 A | 8/1999 | Dogre Cuevas |
| 5,941,844 A | 8/1999 | Eckenhoff |
| 5,957,854 A | 9/1999 | Besson et al. |
| 5,959,529 A | 9/1999 | Kail, IV |
| 6,025,089 A | 2/2000 | Lake |
| 6,030,423 A | 2/2000 | Lake |
| 6,030,721 A | 2/2000 | Lake |
| 6,045,942 A | 4/2000 | Miekka et al. |
| 6,078,842 A | 6/2000 | Gross et al. |
| 6,084,380 A | 7/2000 | Burton |
| RE36,843 E | 8/2000 | Lake et al. |
| 6,136,468 A | 10/2000 | Mitchell, Jr. et al. |
| 6,157,858 A | 12/2000 | Gross et al. |
| 6,186,982 B1 | 2/2001 | Gross et al. |
| 6,187,475 B1 | 2/2001 | Oh et al. |
| 6,200,704 B1 | 3/2001 | Katz et al. |
| 6,208,524 B1 | 3/2001 | Tuttle |
| 6,225,901 B1 | 5/2001 | Kail, IV |
| 6,235,422 B1 | 5/2001 | Kaplan et al. |
| 6,243,192 B1 | 6/2001 | Mitchell, Jr. et al. |
| 6,273,904 B1 | 8/2001 | Chen et al. |
| 6,277,520 B1 | 8/2001 | Moutsios et al. |
| 6,287,721 B1 | 9/2001 | Xie et al. |
| 6,289,238 B1 | 9/2001 | Besson et al. |
| 6,317,630 B1 | 11/2001 | Gross et al. |
| 6,369,793 B1 | 4/2002 | Parker |
| 6,379,835 B1 | 4/2002 | Kucherovsky et al. |
| 6,395,043 B1 | 5/2002 | Shadle et al. |

(56) References Cited

U.S. PATENT DOCUMENTS

| | | |
|---|---|---|
| 6,421,561 B1 | 7/2002 | Morris |
| 6,428,475 B1 | 8/2002 | Shen |
| 6,441,747 B1 | 8/2002 | Khair et al. |
| 6,458,234 B1 | 10/2002 | Lake et al. |
| 6,503,658 B1 | 1/2003 | Klein et al. |
| 6,547,745 B1 | 4/2003 | Rubinstein |
| 6,569,572 B1 | 5/2003 | Ochiai et al. |
| 6,576,364 B1 | 6/2003 | Mitchell, Jr. et al. |
| 6,577,893 B1 | 6/2003 | Besson et al. |
| 6,643,532 B2 | 11/2003 | Axelgaard |
| 6,646,567 B1 | 11/2003 | Olivas |
| 6,653,014 B2 | 11/2003 | Anderson et al. |
| 6,664,006 B1 | 12/2003 | Munshi |
| 6,676,021 B1 | 1/2004 | Luski et al. |
| 6,676,714 B2 | 1/2004 | Langan |
| 6,686,843 B2 | 2/2004 | Felkowitz |
| 6,697,694 B2 | 2/2004 | Mogensen |
| 6,708,050 B2 | 3/2004 | Carim |
| 6,709,778 B2 | 3/2004 | Johnson |
| 6,729,025 B2 | 5/2004 | Farrell et al. |
| 6,740,451 B2 | 5/2004 | Christian et al. |
| 6,743,546 B1 | 6/2004 | Kaneda et al. |
| 6,752,842 B2 | 6/2004 | Luski et al. |
| 6,757,560 B1 | 6/2004 | Fischer et al. |
| 6,794,990 B2 | 9/2004 | Tseng |
| 6,811,308 B2 | 11/2004 | Chapman et al. |
| 6,814,706 B2 | 11/2004 | Barton et al. |
| 6,816,125 B2 | 11/2004 | Kuhns et al. |
| 6,836,215 B1 | 12/2004 | Laurash et al. |
| 6,852,085 B2 | 2/2005 | Rubinstein |
| 6,855,441 B1 | 2/2005 | Levanon |
| 6,884,546 B1 | 4/2005 | Fujita et al. |
| 6,888,502 B2 | 5/2005 | Beigel et al. |
| 6,897,788 B2 | 5/2005 | Khair et al. |
| 6,899,976 B2 | 5/2005 | Larson et al. |
| 6,915,159 B1 | 7/2005 | Kuribayashi et al. |
| 7,015,826 B1 | 3/2006 | Chan et al. |
| 7,017,822 B2 | 3/2006 | Aisenbrey |
| 7,022,431 B2 | 4/2006 | Shchori et al. |
| 7,031,768 B2 | 4/2006 | Anderson et al. |
| 7,043,297 B2 | 5/2006 | Keusch et al. |
| 7,049,962 B2 | 5/2006 | Atherton et al. |
| 7,102,526 B2 | 9/2006 | Zweig |
| 7,187,961 B2 | 3/2007 | Yamashita et al. |
| 7,215,991 B2 | 5/2007 | Besson et al. |
| 7,224,280 B2 | 5/2007 | Ferguson et al. |
| RE39,676 E | 6/2007 | Nitzan |
| 7,238,196 B2 | 7/2007 | Wibaux |
| 7,244,326 B2 | 7/2007 | Craig et al. |
| 7,294,209 B2 | 11/2007 | Shakespeare |
| 7,320,845 B2 | 1/2008 | Zucker |
| 7,335,441 B2 | 2/2008 | Luski et al. |
| 7,340,297 B2 | 3/2008 | Tamarkin et al. |
| 7,340,310 B2 | 3/2008 | Nitzan et al. |
| 7,348,096 B2 | 3/2008 | Schubert et al. |
| 7,354,195 B2 | 4/2008 | Sakano |
| 7,364,896 B2 | 4/2008 | Schembri |
| 7,368,191 B2 | 5/2008 | Andelman et al. |
| 7,383,083 B2 | 6/2008 | Fischer et al. |
| 7,387,607 B2 | 6/2008 | Holt et al. |
| 7,394,382 B2 | 7/2008 | Nitzan et al. |
| 7,448,874 B2 | 11/2008 | Willis |
| 7,474,230 B2 | 1/2009 | Blom et al. |
| 7,483,738 B2 | 1/2009 | Tamarkin et al. |
| 7,491,465 B2 | 2/2009 | Nitzan et al. |
| 7,501,208 B2 | 3/2009 | Feddrix et al. |
| 7,595,723 B2 | 9/2009 | Heitzmann et al. |
| 7,599,192 B2 | 10/2009 | Pennaz et al. |
| 7,603,144 B2 | 10/2009 | Jenson et al. |
| D606,203 S | 12/2009 | Husheer et al. |
| 7,625,117 B2 | 12/2009 | Haslett et al. |
| 7,625,664 B2 | 12/2009 | Schubert et al. |
| 7,643,874 B2 | 1/2010 | Nitzan et al. |
| 7,652,188 B2 | 1/2010 | Levanon et al. |
| 7,688,182 B2 | 3/2010 | Nagai |
| 7,722,248 B1 | 5/2010 | Chapman et al. |
| 7,727,290 B2 | 6/2010 | Zhang et al. |
| 7,768,391 B2 | 8/2010 | Koyama et al. |
| 7,786,847 B2 | 8/2010 | Kang |
| 7,857,507 B2 | 12/2010 | Quinn et al. |
| 7,969,307 B2 | 6/2011 | Peeters |
| 8,029,927 B2 | 10/2011 | Tucholski |
| 8,031,053 B2 | 10/2011 | Greeff |
| 8,079,756 B2 | 12/2011 | Quinn et al. |
| 8,116,841 B2 | 2/2012 | Bly et al. |
| 8,185,341 B2 | 5/2012 | Yarden et al. |
| 8,214,007 B2 | 7/2012 | Baker et al. |
| 8,240,914 B1 | 8/2012 | Chapman et al. |
| 8,249,686 B2 | 8/2012 | Libbus et al. |
| 8,268,475 B2 | 9/2012 | Tucholski |
| RE43,767 E | 10/2012 | Eggers et al. |
| 8,285,356 B2 | 10/2012 | Bly et al. |
| 8,374,688 B2 | 2/2013 | Libbus et al. |
| 8,412,317 B2 | 4/2013 | Mazar |
| 8,441,411 B2 | 5/2013 | Tucholski et al. |
| 2001/0032059 A1 | 10/2001 | Kelly, Jr. et al. |
| 2002/0086215 A1 | 7/2002 | Tamura et al. |
| 2002/0095780 A1 | 7/2002 | Shadle et al. |
| 2002/0110733 A1 | 8/2002 | Johnson |
| 2002/0180605 A1 | 12/2002 | Ozguz et al. |
| 2002/0182485 A1 | 12/2002 | Anderson et al. |
| 2002/0192542 A1 | 12/2002 | Luski et al. |
| 2003/0014014 A1 | 1/2003 | Nitzan |
| 2003/0059673 A1 | 3/2003 | Langan et al. |
| 2003/0082437 A1 | 5/2003 | Sotomura |
| 2003/0165744 A1 | 9/2003 | Schubert et al. |
| 2003/0187338 A1 | 10/2003 | Say et al. |
| 2003/0219648 A1 | 11/2003 | Zucker |
| 2003/0232248 A1 | 12/2003 | Iwamoto et al. |
| 2004/0001998 A1 | 1/2004 | Hopkins et al. |
| 2004/0009398 A1 | 1/2004 | Dorfman |
| 2004/0018422 A1 | 1/2004 | Islam et al. |
| 2004/0170893 A1 | 9/2004 | Nakaishi et al. |
| 2004/0209160 A1 | 10/2004 | Luski et al. |
| 2004/0215098 A1 | 10/2004 | Barton et al. |
| 2004/0217865 A1 | 11/2004 | Turner |
| 2004/0267189 A1 | 12/2004 | Mavor et al. |
| 2004/0267190 A1 | 12/2004 | Tamarkin et al. |
| 2004/0267283 A1 | 12/2004 | Mavor et al. |
| 2005/0013783 A1 | 1/2005 | Perricone |
| 2005/0038473 A1 | 2/2005 | Tamarkin et al. |
| 2005/0085751 A1 | 4/2005 | Daskal et al. |
| 2005/0101843 A1 | 5/2005 | Quinn et al. |
| 2005/0147880 A1 | 7/2005 | Takahashi et al. |
| 2005/0154327 A1 | 7/2005 | Nakazawa |
| 2005/0177064 A1 | 8/2005 | Rubinstein |
| 2005/0194454 A1 | 9/2005 | Ferber et al. |
| 2005/0197540 A1 | 9/2005 | Liedtke |
| 2005/0226310 A1 | 10/2005 | Nakazawa et al. |
| 2005/0260492 A1 | 11/2005 | Tucholski et al. |
| 2005/0267382 A1 | 12/2005 | Church et al. |
| 2006/0001528 A1 | 1/2006 | Nitzan et al. |
| 2006/0007049 A1 | 1/2006 | Nitzan et al. |
| 2006/0012464 A1 | 1/2006 | Nitzan et al. |
| 2006/0122473 A1 | 6/2006 | Kill et al. |
| 2006/0131616 A1 | 6/2006 | Devaney et al. |
| 2006/0159899 A1 | 7/2006 | Edwards et al. |
| 2006/0211936 A1 | 9/2006 | Hu et al. |
| 2006/0227669 A1 | 10/2006 | Pennaz et al. |
| 2006/0253061 A1 | 11/2006 | Anderson et al. |
| 2006/0264804 A1 | 11/2006 | Karmon et al. |
| 2007/0007661 A1 | 1/2007 | Burgess et al. |
| 2007/0011870 A1 | 1/2007 | Lerch et al. |
| 2007/0016277 A1 | 1/2007 | Karat et al. |
| 2007/0020516 A1 | 1/2007 | Yoon |
| 2007/0024425 A1 | 2/2007 | Nitzan et al. |
| 2007/0060862 A1 | 3/2007 | Sun et al. |
| 2007/0066930 A1 | 3/2007 | Tanioka et al. |
| 2007/0208235 A1 | 9/2007 | Besson et al. |
| 2007/0243459 A1 | 10/2007 | Jenson et al. |
| 2008/0007409 A1 | 1/2008 | Ferry et al. |
| 2008/0021436 A1 | 1/2008 | Wolpert et al. |
| 2008/0076974 A1 | 3/2008 | Yamazaki et al. |
| 2008/0091089 A1 | 4/2008 | Guillory et al. |

(56) References Cited

U.S. PATENT DOCUMENTS

| | | |
|---|---|---|
| 2008/0091095 A1 | 4/2008 | Heller et al. |
| 2008/0174380 A1 | 7/2008 | Nitzan et al. |
| 2008/0218345 A1 | 9/2008 | Nitzan et al. |
| 2008/0272890 A1 | 11/2008 | Nitzan et al. |
| 2009/0038746 A1 | 2/2009 | Tucholski |
| 2009/0102611 A1 | 4/2009 | Quinn et al. |
| 2009/0136832 A1 | 5/2009 | Mitsuda et al. |
| 2009/0234200 A1 | 9/2009 | Husheer |
| 2010/0209756 A1 | 8/2010 | Bailey et al. |
| 2010/0245114 A1 | 9/2010 | Celik-Butler et al. |
| 2010/0266895 A1 | 10/2010 | Tucholski |
| 2011/0213559 A1 | 9/2011 | Pollack et al. |
| 2011/0218418 A1 | 9/2011 | Green et al. |
| 2011/0241446 A1 | 10/2011 | Tucholski |
| 2011/0262779 A1 | 10/2011 | Maleki et al. |
| 2011/0274960 A1 | 11/2011 | Ahn |
| 2011/0301493 A1 | 12/2011 | Husheer |
| 2012/0016258 A1 | 1/2012 | Webster et al. |
| 2012/0189038 A1 | 7/2012 | Rofougaran |
| 2012/0203076 A1 | 8/2012 | Fatta et al. |
| 2012/0220835 A1 | 8/2012 | Chung |
| 2012/0229270 A1 | 9/2012 | Morley et al. |
| 2012/0316455 A1 | 12/2012 | Rahman et al. |
| 2012/0316456 A1 | 12/2012 | Rahman et al. |
| 2012/0316457 A1 | 12/2012 | Meng et al. |
| 2012/0316458 A1 | 12/2012 | Rahman et al. |
| 2013/0030259 A1 | 1/2013 | Thomsen et al. |
| 2013/0074330 A1 | 3/2013 | Tucholski |
| 2013/0323565 A1* | 12/2013 | Tucholski ............... H01M 6/40 429/127 |
| 2014/0121557 A1 | 5/2014 | Gannon et al. |

FOREIGN PATENT DOCUMENTS

| | | |
|---|---|---|
| EP | 0862227 A1 | 9/1998 |
| EP | 1026767 A1 | 8/2000 |
| EP | 1096589 A1 | 5/2001 |
| EP | 1107336 A2 | 6/2001 |
| EP | 2003940 A2 | 12/2008 |
| JP | 55-133770 A | 10/1980 |
| JP | 58-206048 A | 12/1983 |
| JP | 59-228353 A | 12/1984 |
| JP | 61-55866 A | 3/1986 |
| JP | 61-64077 A | 4/1986 |
| JP | 62-126557 A | 6/1987 |
| JP | 62-165875 A | 7/1987 |
| JP | 62-165876 A | 7/1987 |
| JP | 62-285954 A | 12/1987 |
| JP | 63-81762 A | 4/1988 |
| JP | 63-119155 A | 5/1988 |
| JP | 64-24364 A | 1/1989 |
| JP | 2-273464 A | 11/1990 |
| JP | 4-276665 A | 10/1992 |
| JP | 5-217587 A | 8/1993 |
| JP | 5-225989 A | 9/1993 |
| JP | 5-275087 A | 10/1993 |
| JP | 2000-164033 A | 6/2000 |
| JP | 2000-229128 A | 8/2000 |
| JP | 2000-319381 A | 11/2000 |
| JP | 2001-23695 A | 1/2001 |
| JP | 2001-521676 A | 11/2001 |
| JP | 2003-151634 A | 5/2003 |
| JP | 2003-282148 A | 10/2003 |
| JP | 2004-336240 A | 11/2004 |
| JP | 2005-39256 A | 2/2005 |
| JP | 2006-039789 A | 2/2006 |
| JP | 2010-197254 A | 9/2010 |
| JP | 2012-7963 A | 1/2012 |
| JP | 2012-207943 A | 10/2012 |
| KR | 10-1149809 B1 | 5/2012 |
| TW | 540185 B | 7/2003 |
| WO | 96/38867 A1 | 12/1996 |
| WO | 97/17735 A1 | 5/1997 |
| WO | 98/22987 A2 | 5/1998 |
| WO | 98/48469 A1 | 10/1998 |
| WO | 00/17950 A1 | 3/2000 |
| WO | 00/36672 A1 | 6/2000 |
| WO | 03/069700 A2 | 8/2003 |
| WO | 2006/003648 A2 | 1/2006 |
| WO | 2012/057931 A1 | 5/2012 |

OTHER PUBLICATIONS

Acheson Industries, "Acheson Electrical Materials," from www.achesonindustries.com, last accessed Nov. 24, 2009.

Advanced Coatings and Chemicals, "Technical Data Sheet," Temple City, CA, last accessed Nov. 24, 2009.

Cambridge Temperature Concepts Limited, DuoFertility Monitor, accessed at www.duofertility.com/what-is-duofertility/duofertility-monitor on Apr. 1, 2013, 3 pages.

Dolan, B., "Wireless health opportunity begins at conception," http://mobihealthnews.com/11042/wireless-health-opportunity-begins-at-conception/, May 26, 2011, 9 pages.

Dolan, B., "Duofertility wireless sensor receives FDA clearance," http://mobihealthnews.com/16028/duofertility-wireless-sensor-receives-fda-clearance/, Jan. 20, 2012, 9 pages.

Hartman, Lauren R., "Flexibles stay resilient," Packaging Digest, Mar. 1, 2005.

Linden, D., Handbook of Batteries and Fuel Cells, pp. 5.5-5.7, McGraw-Hill, Inc., 1984.

Linden, D., Handbook of Batteries, Second Edition, pp. 8.8-8.9, McGraw-Hill, Inc., 1995.

Omnexus Adhesives & Sealant Solutions, "Ethylene Vinyl Acetate (EVA) and Other Hot Melts," from http://www.omnexus4adhesives.com/bc/construction-channel/index.aspx?id=ethylene, last accessed Aug. 11, 2010.

Prima-Temp Inc., Device Brochure and Descriptive Pamphlet for Real-Time Wireless Core Temperature Monitoring, Feb. 21, 2012, 3 pages.

U.S. Appl. No. 13/899,291 for Multi-Cell Battery to Tucholski, filed May 21, 2013.

International Search Report and Written Opinion issued Sep. 26, 2013 in corresponding PCT Patent Application No. PCT/US2013/047618.

International Search Report and Written Opinion from Corresponding Application No. PCT/US2014/072997, Dated Sep 15, 2015.

* cited by examiner

BODY TEMPERATURE LOGGING PATCH

CROSS-REFERENCE TO RELATED APPLICATIONS

Not applicable.

BACKGROUND OF THE INVENTION

In the past 100 years or so, electrical or electronic circuits, have seen a dramatic change in their design and their assembly process. About 100 years ago, DC powered circuits were hard wired and hand soldered in a box format. The high current electronic or electrical components were fastened to the box and then they were manually connected by hand soldering wire of sufficient diameter to carry the required currents and voltages. In many of these circuits the large sized, multi voltage batteries were placed in a battery compartment and then they were also hand soldered into the circuit. Typical battery sizes could be a 6 volt lantern battery or a battery pack made of multiple 6" size unit cells or even possibly some smaller sizes. When the batteries were depleted, they were desoldered and replaced in the same manner as when the circuit was made.

About 60 years ago with the invention of the transistor and other electronic parts, the design and manufacturing of circuits changed drastically. Due to the electronic changes, which required much lower currents and many times lower voltages, circuits could be made in a more efficient and compact manner. This allowed circuits to be made on a circuit board in a wave soldering method. As part of this wave soldering assembly method, battery holders were also included into the circuit. Due to the big reduction in required voltages and currents the power source size could also be reduced in size. Typical power sizes could now be D, C, AA, AAA, transistor 9 volt battery or even coin or button cells. In these new circuits with the battery holder, the consumer could install the battery when he begins using the device as well making it very easy to replace the depleted batteries.

In recent years, as described in several Blue Spark patent applications, printed electronics on flexible substrates has become a new process and is growing in popularity. In this process, some or all of the circuit is printed as well as some of the electronic components. Typically this type of circuit could include a display, IC chip, sensor, antennae, lights and a relatively low capacity power source such as a flat printed battery. In some applications, the power source could also be printed in a totally integrated manner.

Alternatively, the power source can be integrated in a different manner. In order to reduce costs, the power source can be a printed or otherwise constructed as a flat battery that is provided as a complete cell for later integration into the desired circuit. A typical cell can provide, for example, about 1.5 volts DC. Where greater voltages are required, it is conventionally known to connect two or more cells in series to increase the voltage. Similarly, multiple cells can be connected together in parallel to increase the effective capacity. For example, a battery can include two cells electrically connected in series to provide 3 volts DC. Still, it is desirable to reduce the overall size of the battery, even with multiple cells, for use in small circuits. Various designs and methods of manufacture of a flat cell and batteries are described in co-pending U.S. application Ser. No. 11/110,202 filed on Apr. 20, 2005 now issued U.S. Pat. No. 8,722,235, Ser. No. 11/379,816 filed on Apr. 24, 2006 now issued U.S. Pat. No. 8,722,233, Ser. No. 12/809,844 filed on Jun. 21, 2010 now issued U.S. Pat. No. 8,574,754, Ser. No. 13/075,620 filed on Mar. 30, 2011 (Abandoned), Ser. No. 13/625,366 filed on Sep. 24, 2012, and Ser. No. 13/899,291 filed on May 21, 2013 now issued U.S. Pat. No. 8,765,284, as well as issued U.S. Pat. Nos. 8,029,927, 8,268,475, 8,441,411, all of which are incorporated herein by reference.

In recent years there has been a growing interest for active medical technologies that can leverage the increasing power of portable computers, smartphones, and tablets. One such example includes a Body Temperature Logging patch ("patch") that will be worn on the body and will track and collect in memory the temperature of the patient's body over time. Conventional body temperature devices today take a measure of the body temperature at only a single point in time. In contrast, the patch device described herein can be applied as a patch and worn over a lengthy period of time, such as a 24 hour period (although longer or shorter time periods are contemplated). The patch preferably includes medical skin-contact approved adhesive that is suitable for application to the skin of a user, though various generally flexible and compressive materials can be utilized. In addition or alternatively, the patch may include the ability to sense various other phenomena, such as through multiple sensors. For example, the patch could sense any or all of: multiple temperatures of the patient at the same or different locations, the patient's pulse, blood-oxygen levels, EKG, ambient temperature, ambient humidity, ambient pressure, ambient light, sound, and/or radiation levels, patient bodily functions, time, patient movement (e.g., via an accelerometer), etc.

SUMMARY OF THE INVENTION

The following presents a simplified summary of the invention in order to provide a basic understanding of some aspects of the invention. This summary is not an extensive overview of the invention. It is intended to identify neither key nor critical elements of the invention nor delineate the scope of the invention. Its sole purpose is to present some concepts of the invention in a simplified form as a prelude to the more detailed description that is presented later.

In accordance with one aspect of the present application, an actively-powered temperature data logger patch is provided with wireless data communication. A first substrate layer comprises a first end and a second end. A sealed, flexible battery comprises a printed electrochemical cell with an anode and a cathode, at least one of said anode and cathode being formed of a cured or dried ink, and first and second battery electrode contacts that are each electrically coupled to one of the anode and cathode. A flexible circuit comprises a microprocessor, a temperature sensor configured to sense a temperature of a target subject, a wireless communication transmitter and an antenna. The flexible circuit further comprises first and second battery contact pads that are each electrically coupled to one of the first and second battery electrode contacts to thereby electrically power the microprocessor, wireless communication transmitter, and temperature sensor. The temperature sensor is located at the first end of the first substrate layer, and the antenna is located at the second end of the first substrate layer. A second substrate layer comprises an adhesive configured to be removably applied to a surface of the target subject. The flexible battery and flexible circuit together comprise an electronics inlay that is arranged in a covering, stacked arrangement between the first and second substrate layers. All of the first substrate layer, electronics inlay, and second substrate layer are flexible and configured to conform to a curved surface of the target subject.

In accordance with another aspect of the present application, an actively-powered temperature data logger patch is with of wireless data communication is provided. A first substrate layer comprises a first end and a second end. A plurality of sealed, flexible batteries in a parallel arrangement, each battery comprising a printed electrochemical cell with an anode and a cathode that are provided in a co-planar arrangement and an aqueous electrolyte layer substantially covering and in electrical contact with said anode and cathode. A flexible circuit comprises a microprocessor, a temperature sensor configured to sense a temperature of a target subject, a wireless communication transmitter and an antenna. The flexible circuit further comprises a pair of contact pads that are each electrically coupled to one corresponding contacts of the plurality of flexible batteries to thereby electrically power the microprocessor, wireless communication transmitter, and temperature sensor. All of the microprocessor, temperature sensor, and wireless communication transmitter actively receive active electrical power from the flexible batteries. A second substrate layer comprises an adhesive configured to be removably applied to a surface of the target subject. The flexible battery and flexible circuit are disposed between the first and second substrate layers, and all of the first substrate layer, electronics inlay, and second substrate layer are flexible. A switch is used to activate the microprocessor to an operational power state and thereby enable active electrical power to the microprocessor, temperature sensor, and wireless communication transmitter only when a user intends to begin use of the patch.

BRIEF DESCRIPTION OF THE DRAWINGS

The foregoing and other features and advantages of the present invention will become apparent to those skilled in the art to which the present invention relates upon reading the following description with reference to the accompanying drawings, in which.

DETAILED DESCRIPTION OF EXAMPLE EMBODIMENTS

Figure 1:
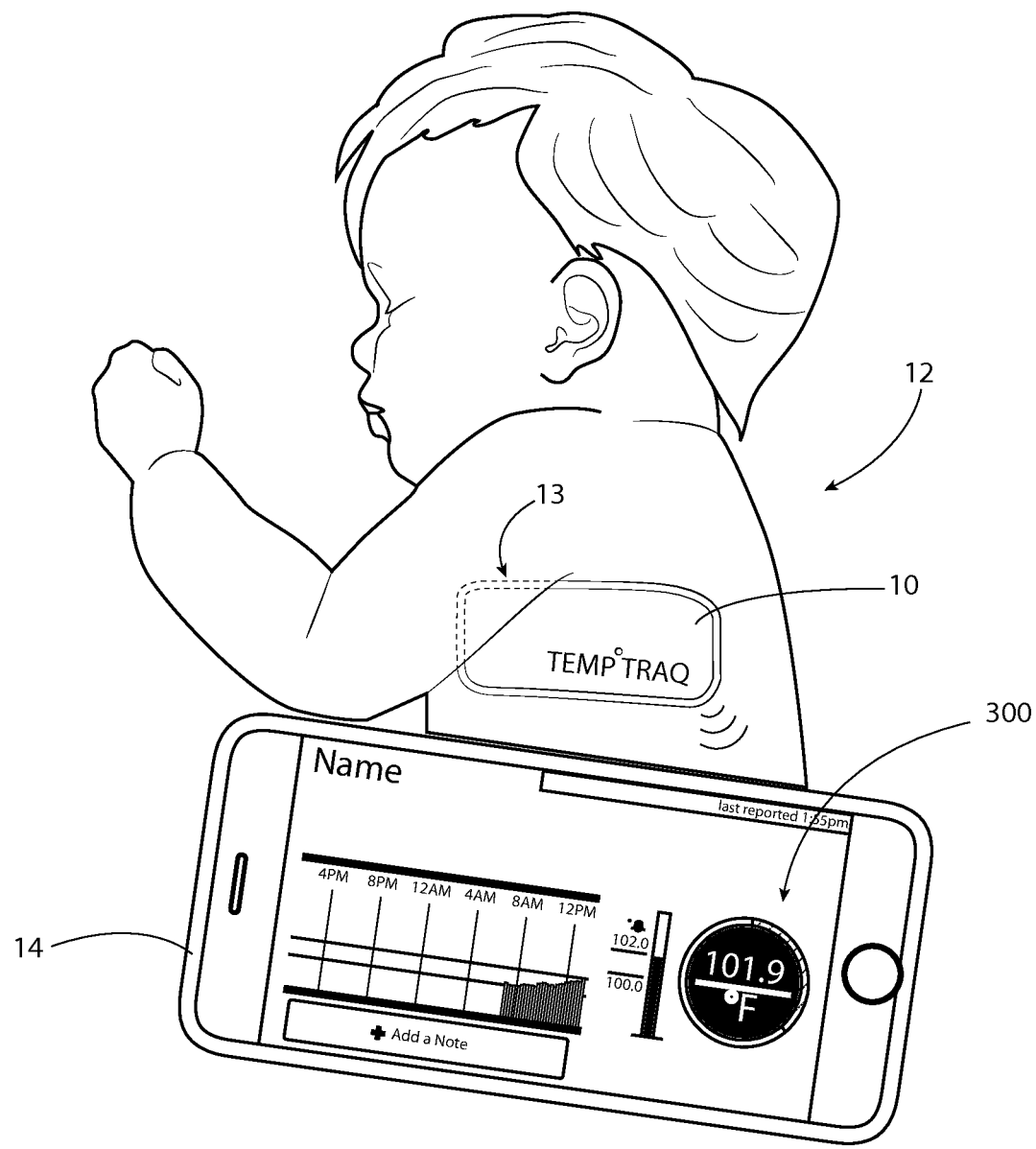
FIG. 1 illustrates a perspective view of an example patch attached to a person for measuring body temperature using an example smartphone.

In the instant application, a Body Temperature Logging Patch ("patch") is described that will be worn on the body and will track and collect in memory the temperature of the patient's body over time. The patch is intended to be a one-time use, disposable patch. For example, as shown in FIG. 1, the patch 10 can be worn on the body of a patient 12, such as on the torso and adjacent to the underarm location 13 (i.e., the armpit or axillary region). It could also be worn at other locations, such as on the forehead, other torso locations, arm, leg, or other on-body location. Conventional body temperature devices today take a measure of the body temperature at only a single point in time. In contrast, the patch 10 device described herein can be applied as a patch and worn over a lengthy period of time to provide a large number of measurements, such as a 12, 16, or 24 hour period (although longer or shorter time periods are contemplated). The patch 10 preferably includes a medical skin-contact approved adhesive that is suitable for application to the skin of a user, though various generally flexible and compressive materials can be utilized. In addition or alternatively, the patch 10 may include the ability to sense various other phenomena, such as through multiple sensors. For example, the patch 10 could sense any or all of: multiple temperatures of the patient at the same or different locations, patient's pulse, blood-oxygen levels, EKG, ambient temperature, ambient humidity, ambient pressure, ambient light, sound, and/or radiation levels, patient bodily functions, time, patient movement (e.g., via an accelerometer), etc.

At any time while the patch 10 is being worn by a patient, such as during the described 24 hour period, the patch can be read remotely (though in relatively close proximity to the body) by a computing device 14, such as a portable computer, smart phone, tablet, and/or other sensor device that is enabled with the same or compatible radio communication protocol of the patch 10. As shown herein, the computing device 14 is shown as a smart phone, though it is understood that it can be a portable computer, smart phone, tablet, and/or other sensor device configured to communicate with the patch 10 via radio communication. The computing device 14 comprises a programmable microprocessor capable of running applications, a power supply (battery or AC line power), a display, and a transceiver capable of either one-way communication (i.e., receive only) or two-way communication (send and receive) with the patch 10. Additionally, the computing device 14 preferably is capable of communication on a local network (LAN) or wide-area network (WAN), including the internet and world-wide web. The temperature measurements can be taken on-demand and/or at pre-set intervals, and can be stored locally in the memory of the patch 10 and/or in the memory of the reading device (e.g., smartphone, tablet, portable computer, sensor, etc.).

In one example embodiment, the patch 10 can utilize the Bluetooth radio protocol, and preferably the Bluetooth Low Energy (BTLE, or sometimes referred to as Bluetooth Smart) radio protocol, which is aimed at very low power applications. Thus, the patch 10 can communicate with a standard smart phone (or computer, tablet, sensor, etc.) that is enabled with a compatible Bluetooth radio. Bluetooth is a set of standards for smartphones and similar devices to establish wireless radio communication with each other in relatively close proximity. Bluetooth operates in the 2.4 GHz short-range frequency band, and more specifically in the range of 2400-2483.5 MHz. A typical range for a Bluetooth radio is up to 100 meters (Class 1) and up to 30 meters (Class 2). A typical range for a BTLE radio can be similar, although the over the air data rate and application throughput rates are less. In the instant application, the range for the BTLE radio is expected to be in the range of 10-30 meters, although this could be increased or decreased. Because it is a radio-based system, the transmitter and receiver do not have to be in visual line-of-sight, although a wireless path must be viable. Additionally, various implementations of the Bluetooth protocol can include transmit only, receive only, or transmit and receive. For example, one embodiment of the instant application includes a transmit-only temperature logging patch, although other embodiments could receive. Finally, Bluetooth/BTLE is an active radio system, meaning that it requires a local active power supply to transmit and/or receive data. A battery, such as that described herein, is a common example.

In another example embodiment, the patch 10 can include a High Frequency/Near Field Communication (NFC) radio protocol. It is contemplated that the patch 10 can include the NFC radio in combination with the Bluetooth radio, or even as a standalone radio system. Thus, this patch 10 could be read by a standard smart phone (or computer, tablet, sensor, etc.) that is enabled with a compatible High Frequency/Near Field Communication NFC and ISO-15693 RFID radio protocol. For example, if a person who is wearing the patch 10 is sleeping, another person with a smart phone would be able to read the output of the patch 10 with a High Frequency/Near Field Communication NFC and ISO-15693 RFID enabled smart phone. Near field communication (NFC) is a set of standards for smartphones and similar devices to establish radio communication with each other by touching them together or bringing them into close proximity, usually no more than a few centimeters (although it is contemplated that the range could be increased). NFC standards cover communications protocols and data exchange formats, and are based on existing radio-frequency identification (RFID) standards including ISO/IEC 14443, ISO/IEC 15693 and FeliCa. The standards include ISO/IEC 18092 and 21481, and those defined by the NFC Forum. NFC is a set of short-range wireless technologies, typically requiring a distance of 4 cm or less. NFC operates at 13.56 MHz on ISO/IEC 18000-3 air interface and at rates ranging from 106 kbit/s to 424 kbit/s. NFC involves an initiator and a target, where the initiator actively generates an RF field that can power a passive target.

Regardless of the wireless communication system used, the person (or automated device) reading the temperature information would not have to wake up the patient 12 wearing the patch 10 and would instantly, such as through a smart phone app (Application) or the like, be able to both graphically and/or in a text-based format (e.g., list, table, chart, etc.) display the instant body temperature and/or history of the person wearing the patch for some or all of time they have been sleeping or otherwise wearing the patch. This display of information allows for the trend history of the body temperature. The Application functionality may include, but is not limited to, some or all of the following features:

Enable the Smart phone to create a data link to the patch;
Read the unique identifier code programmed into the Integrated Circuit;
Read the time tagged temperature data stored in memory of the integrated circuit, including a portion of the data or even all of the data since the patch was activated;
Read a battery voltage level, estimate a battery voltage level, or estimate an amount of time remaining for patch operation;
Convert Temperature data from Fahrenheit to Celsius or from Celsius to Fahrenheit, or other temperature units;
Graphically display the temperature data versus time with multiple graph display choice (i.e., Line graph, Bar chart, etc.);
Display the temperature versus time data in tabular form;
Perform data analysis;
Set alarm levels for temperatures that are near or exceed a pre-set boundary condition, signal alarms via visual and/or audible methods;
Annotate a graphical chart of the temperature data with automatic or manually-input information, or a combination thereof, to link a particular temperature and/or time data point with additional information for later reference;
Saving historical data;
Creating multiple user profiles;
Allow for a link to the integrated circuit unique identifier to a user profile;
Email, texting or other transmission of data to third party;
Re-Order additional patches online; and
Link to Websites for medical advice or medical contact information.

If the patch is enabled for two-way communication, the Application functionality may also include the following features:

Send an initialization (or re-initialization) command to the patch, and set a flag that the electronics were successfully initiated; and
Send data to the patch, including initialization of a time stamp to begin data logging, data sensing time interval, data retrieval time interval, data format, an upper temperature boundary level, a lower temperature boundary level, etc.

The wireless radio protocol can enable the smart phone (or computer, tablet, sensor, etc.) to download temperature data on-demand and/or download some or all stored data from the patch. In addition or alternatively, the computing device 14 (e.g., smartphone, computer, tablet, other sensor device, etc.) can be configured to download and utilize data from one or more patches and/or other local sensor(s). In addition or alternatively, the Smart Phone App (Application) or the like can be configured to utilize some or all of the data collected and apply analytics thereto for determining data trends, relationships, etc.

It is understood that while the Bluetooth wireless protocol has primarily been described herein, various other wireless protocols can also be used, including standards-based protocols and even proprietary protocols. Example protocols can include any or all of the following (or even others, without limitation): NFC, RFID, Wifi, Cellular (analog or digital, including all past or present iterations), ZigBee, RuBee, etc. Indeed, certain wireless options such as Bluetooth/Bluetooth LE or NFC with extremely simple setup can be used to bootstrap more capable wireless connections, despite a relatively low-speed connection.

Figure 2:
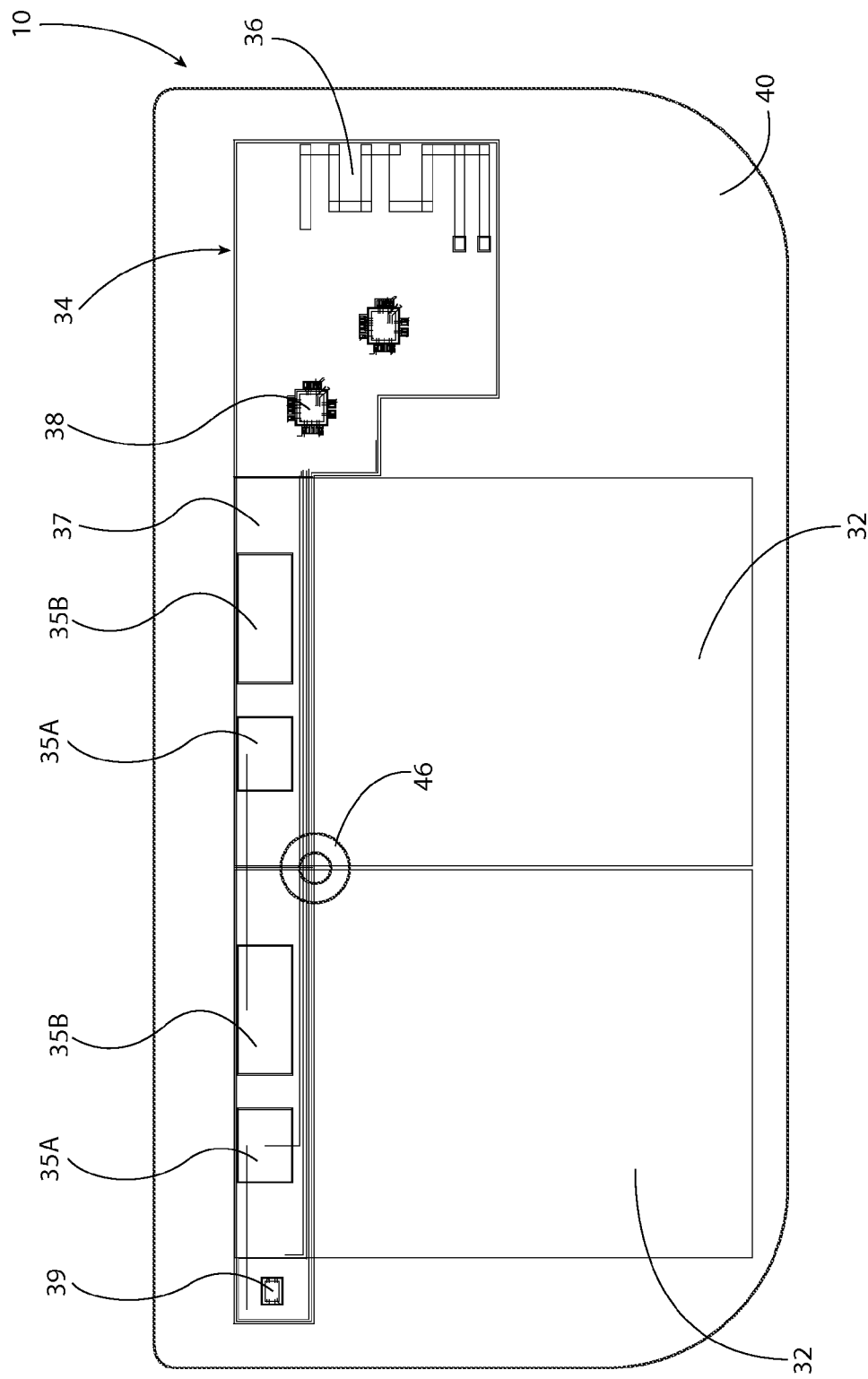
FIG. 2 illustrates a top schematic view of the example patch with a top layer removed.
Figure 3:
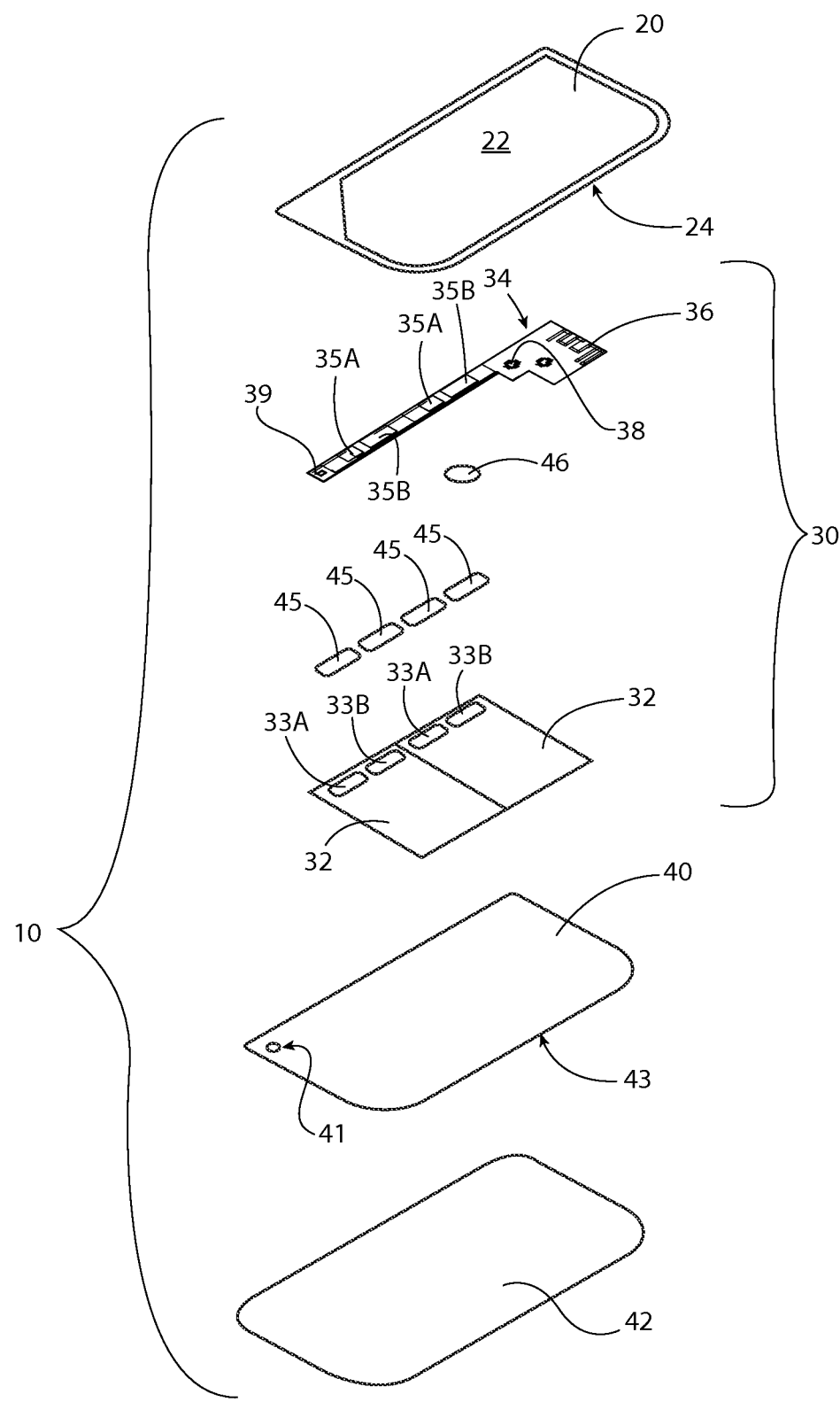
FIG. 3 illustrates an exploded view of one embodiment of the example patch.

Turning now to FIGS. 2-3, one example construction of the patch 10 will be described. The patch 10 can include the following layers arranged in a covering, stacked arrangement: (A) Flexible single sided adhesive 20, where the non-adhesive side 22 is preferably a material on which a printing process can be completed and the opposite adhesive side 24 is coupled to the next layer; (B) Electronics Inlay 30, which can include the following components in various orders: (a.) Flexible, printed battery 32 with battery electrodes 33A, 33B (one or more batteries, two are shown in the example); (b.) Flexible circuit 34 (printed or etched or laminated) with battery contact pads 35A, 35B; (c.) Antenna 36; (d.) Integrated Circuit 38 with capability to interface with wireless communication protocols (e.g., Bluetooth, HF/NFC, RFID or other) using an on-board or separate communications chip, and capability to interface with an onboard or separate sensor to obtain temperature readings and store these reading and time-associated data of the reading in onboard memory; and (e.) Temperature sensor 39 in communication with the integrated circuit 38; and (C) Double-sided adhesive 40 with a release liner 42, where one side 43 (e.g., the outwardly-facing side) of the adhesive 40 is preferably a skin-contact approved adhesive. For example, once completed the patch 10 can have a single removable layer as the release liner 42, which is removed by the patient immediately prior to adhering the patch 10 onto the skin.

The flexible circuit 34 can have various geometries, and can have the different elements arranged variously thereon. Preferably, temperature sensor 39 is located at a first end of the patch 10, while the antenna 36 is located at an opposite, second end of the patch 10. One example is shown in FIG. 2, in which the flexible circuit 34 has a generally "L"-shaped geometry that extends along the longitudinal axis of the patch 10. The temperature sensor 39 is located at the left-hand side, preferably along the left-hand edge of the patch 10, while the antenna is located on the opposite right-hand side, preferably along the right-hand edge of the patch 10. The separation of the temperature sensor and the antenna provides the benefit of enabling each element to be positioned at an optimized location for their function while the patch 10 is in use on the patient's body. For example, as shown in FIG. 1, placement of the temperature sensor 39 on the left-hand side of the patch places the sensor in a position to be directly at the underarm location (i.e., the armpit or axillary region). This enables the temperature sensor 39 to be in a prime position to obtain temperature data. Additionally, placement in the upper left-hand corner of the patch 10 also provides an easy to understand location to help the user understand where the temperature sensor 39 is with respect to the patient's underarm. At the same time, placement of the antenna 36 at the right-hand side of the patch places the antenna in an unobstructed position to transmit a wireless radio signal to the computing device 14. Thus, the antenna 36 is not obstructed by the patient's arm or underarm, but is instead located outwards to provide increased radio signal strength, which can increase the radio range as well as the data throughput. It is further contemplated that the patch 10 could have various other geometries and arrangements of the temperature sensor and antenna, depending upon the desired use case and placement on the patient's body.

The batteries 32 and integrated circuit 38 are located in between. The portion of the flexible circuit 34 that includes the antenna 36 and integrated circuit 38 can have a relatively small size, such as a 20 mm×20 mm size with a thickness of less than 1 mm (e.g., such as 0.8 mm or less), although various sizes are contemplated. Still, the remainder of the flexible circuit 34 that includes the battery contact pads 35A, 35B and the temperature sensor 39 can be relatively larger. It is understood that the various layers can include adhesives therebetween, such as pressure-sensitive adhesives that can have release liners to facilitate manufacturing. For example, it is contemplated that some or all of the various layers 20, 32, 34, 39, 40 can be manufactured separately, and then later assembled together. For example, both of the batteries 32 and the flexible printed circuit 34 can be manufactured separately, and assembled together to manufacture the patch 10. The pressure-sensitive adhesives can be attached to some or all of the various layers. Alternatively, the various layers can be coupled together in various other manners, such as via glues, welding, other adhesives, etc.

In other example embodiments, the patch 10 can include additional or alternative layers that can provide additional features, such as facilitating adhesion of the patch 10 to the skin of a patient. For example, the flexible single sided adhesive 20 could include a coated, non-woven PSA tape 44, including a relatively high performance medical grade adhesive system intended for direct skin contact applications, and is preferably constructed with a permanent adhesive that exhibits excellent wetout to a variety of substrates. In addition to the double-sided adhesive 40, a further double-sided adhesive layer (not shown) could be used to facilitate adhering the patch 10 to the skin of the patent.

In one example, some or all of the double-sided adhesive 40 could include a hydrogel, which is a material comprising polymer chains that are hydrophilic and exhibit a degree of flexibility very similar to natural tissue or skin. Various types of hydrogels could be used, and may include any or all of water, glycerol, acrylate/acrylamide co-polymer, and/or other elements. Preferably, the hydrogel provides excellent skin-adhesion properties, while also providing desired thermal conductivity properties to act as a thermal conduit between the temperature sensing abilities of the flexible circuit 34 and the patient's skin. Regarding the additional double-sided adhesive layer, it is contemplated that such an adhesive could be useful for facilitating and maintaining adhesion of the patch 10 to the patient over a predetermined time period, such as 12, 16, 24, or 48 hours, etc. For example, initial hydrogel adhesion may be poor, as hydrogel adhesion gradually improves after it is applied to skin as it warms up to body temperature and begins creep flow to make intimate contact with the skin surface. Thus, the additional adhesive layer can provide an immediate initial adhesive bond to allow the hydrogel enough time to for a suitable bond to the skin.

Various materials could be used for the double-sided adhesive layer, such as a cross-linked close-cell polyethylene foam coated on either or both sides with a pressure-sensitive adhesive that provides an adhesion of at least approximately 50 grams per inch, although greater or lesser adhesion amounts are contemplated. Such a foam may also provide insulation from the temperature sensor to the ambient surroundings to thereby help with temperature accuracy. Preferably, the material is capable of providing resistance to water, sweat, humidity, or other human or environmental factors that may otherwise reduce or deteriorate the bond between the patch 10B and the skin of the patient over the length of the predetermined time period.

Additionally, the hydrogel could be coated on the underside of the double-sided adhesive layer, or could be provided in a recess or even a through hole of the adhesive layer. For example, the double-sided adhesive layer 40 can include a hole extending therethrough, and the hydrogel can be partially or completely located within the hole such that the hydrogel and adhesive layer 40 are substantially co-planar. It is further contemplated that the hydrogel can be provided directly to the adhesive layer 40, or could even be provided to the electronics inlay (such as about the temperature sensor) and thereby indirectly provided to the adhesive layer. It is contemplated that the hydrogel layer could cover a relatively large or small portion of the patch 10. For example, it is contemplated that the hydrogel layer could be used to increase thermal conductivity between the temperature sensor of the flexible circuit 34 and the user's skin. Thus, the hydrogel layer could be reduced in size to approximately the size of, and located directly over, the temperature sensor. Such a construction could more closely focus the thermal detection abilities of the temperature sensor, provide increased adhesion abilities of the one or more adhesive layers, and/or provide greater protection for the flexible circuit 34 and/or flexible battery 32. Regarding the removable release liner 49, it may include various easily removable liners, and preferably a liner that is compatible and easily removable from the hydrogel and adhesive 40, such as polyolefin-coated or silicone-coated coated papers and films.

It is preferable that all of the layers used herein are flexible, able to be adhered to curved and/or variable surfaces (e.g., a patient's skin) for a lengthy period of time, able to flex and move with the movement of the patient, and be comfortable to wear. It is contemplated that the flexible patch, including the flexible batteries and the flexible circuit, can be stretched, wrinkled, bent, or flexed without degradation of the batteries and circuit, or active operation thereof. Preferably, the patch 10 can obtain a relatively flexible curvature radius, such as at least a 35 mm radius of curvature, measured along either axis (i.e., along the longitudinal axis and/or the transverse axis). Along these lines, it is contemplated that the patch 10 will be of a size (or multiple sizes) suited for use on the desired location of the body. In one example, for use at the underarm location (i.e., the armpit or axillary region), the patch 10 can have an overall dimension of about 2 inches by 4 inches (50 cm by 100 cm), although various sizes are contemplated. Similarly, the patch 10 has a relatively thin profile, on the order of 2 mm -4 mm thick. The beneficial design of the flexible circuit, flexible batteries, and overall flexibility of the complete assembled package provides a comfortable patch that can be easily worn by patients of all ages (babies through adults) while awake, moving, or sleeping.

In addition or alternatively, either or both of the outer layers 20, 42 can include a printable surface to provide indicia, instructions, or even an identification location for the antenna 36 (e.g., a visual target to help a user obtain successful communication with the computing device 14) and/or temperature sensor 39. For example, as shown in FIG. 3, the indicia could include a triangle shape, an arrow and/or wording (e.g., "underarm") to tell the user which corner of the patch 10 should be positioned at the underarm location (i.e., the armpit or axillary region). Similarly, indicia could be provided at the other end of the patch 10 located about the antenna 36, so that the user knows to keep this portion of the patch exposed for increased radio signal strength. It is contemplated that some or all of the layers of the patch 10 can be exposed to the external environment, or alternatively some of the layers could be shielded or protected from the external environment. In one example, the electronics inlay can be encapsulated between the outer layers (e.g., layers 20 and 40) for protection. Finally, various adhesive layers, etc. can be provided between any or all of the various layers discussed above.

The various parts of the electronic inlay 30 will now be discussed in greater detail. It is understood that the electronic inlay 30 can be used together with the described embodiment of the patch 10, or even other variations thereof. As described above, the electronics inlay 30 includes a flexible printed circuit 34 that can include an antenna 36 for wireless communication (and/or power transfer, if used with NFC, RFID, or similar), and an integrated circuit 38. The flexible printed circuit 34 can also include battery contact pads 35A, 35B adapted to be electrically coupled to corresponding battery electrodes 33A, 33B of the printed batteries 32. In the shown example, two batteries 32 are arranged in a serial configuration to provide increased voltage, and the flexible printed circuit 34 includes suitable contacts and traces for power transfer. Still, it is understood that one battery, or more than two batteries, could be used. In one example construction, an etched copper circuit can be provided on a substrate 37, such as a polyester or polyimide substrate about 0.002" thick. It is contemplated that the substrate 37 can be flexible or rigid, although it is preferably flexible. The copper circuit is being used only as an example for this method of cell/battery attachment and it could be used with any commercial circuit material such as etched aluminum or printed carbon, silver, or any other metallic substrate etc. The circuitry can provide electrical communication among the various components on the substrate 37, and also provide a connection to the flexible batteries 32. Preferably, the etched copper circuit is a multi-layer board having traces at least on both sides, and possibly containing layered traces.

Additionally, circuit sub-assembly contacts can be provided as well as about 0.002" thick non-conductive pressure sensitive adhesive (PSA) that can be applied over the electrical component (including processor and antenna) and the substrate. The PSA layer can have an example thickness a range of about 0.0005-0.005", and can have a size similar to the size of the power source used (e.g., a single cell or multiple cells). It is further contemplated that the power source (e.g., batteries 32) could be printed onto the substrate, or could be later attached as a completed unit cell(s). In the shown example, the substrate 37 extends primarily across the top and right-hand side of the patch 10, while the batteries 32 occupy most of the central and left-hand side of the patch 10. This configuration provides an increased, such as maximized, space availability to use relatively larger batteries with relatively larger electrical capacities. Although there may be overlap where the batteries 32 physically interface with the substrate 37 via the battery contact pads 35A, 35B, it is generally contemplated that, in the assembled state, the majority of the substrate 37 will be co-planar with the majority of the batteries 32. Conductive pads 45 can be used to connect the battery contacts 33A, 33B to the battery contact pads 35A, 35B of the substrate 37. In other examples, the batteries 32 could also be mechanically and electrically coupled to the circuit 34 by conductive adhesive, conductive ink, and/or by ultrasonic welding of the battery electrodes 33A, 33B to the battery contact pads 35A, 35B. In addition or alternatively, a pressure sensitive adhesive or the like could provide additional coupling between the batteries 32 and the substrate 37. Although various configurations are contemplated, the battery contact pads 35A, 35B could be located on an underside surface of the substrate 37 (e.g., a bottom side of the flexible printed circuit 34). Indeed, in one configuration, all of the battery contact pads 35A, 35B, antenna 36, integrated circuit 38, and temperature sensor 39 could be arranged on an underside surface of the substrate 37 (e.g., a bottom side of the flexible printed circuit 34, as viewed in the normal operational use condition). Still, some or all of these components could be on the upper side of the substrate 37. Finally, it is contemplated that the batteries 32 could even be printed on the same substrate as the flexible printed circuit 34 (including either or both of the antenna 36 and integrated circuit 38). Such a construction could place the battery 32 on the same side or opposite side of the common substrate as the flexible printed circuit 34.

In addition or alternatively, a switch 46 could be used to activate the circuit 38 only when a user intends to use the patch 10, which can conserve battery power during extended storage. Various example switches 46 could be used to enable activation of the integrated circuit 38, such as a momentary dome switch, a toggle switch or even a one-time switch. In one embodiment, the switch 46 could be a momentary dome switch that is used to activate a latching power circuit, which will in-turn enable electrical communication between the battery and the integrated circuit 38 to thereby activate the integrated circuit 38 from a reduced power state to an operational power state. The latching power circuit is in electrical communication between the battery and could remain in a super low-power state that only senses the actuation of the dome switch 46. The main integrated circuit 38 could preferably remain in a zero power state, or possibly a reduced power state (i.e., a very low power state). The use of a latching power circuit could thereby avoid power drain by the integrated circuit 38, communication circuit, and temperature sensor to enable the patch 10 to have a useful shelf life of many years, such as 2-3 years or even more. The latching power circuit could have electrical traces in line with the dome switch 46, such that the momentary actuation of the switch 46 by the user is sensed by the latching power circuit, which then wakes up the integrated circuit 38 from a reduced power state to a regular operational state by enabling electrical communication with the battery to activate the patch 10.

Preferably, the switch 46 is arranged on an upper surface of the substrate 37 (e.g., a top side of the flexible printed circuit 34, as viewed in the normal operational use condition) so that it can be readily operated by a user of the patch 10. As an alternative to the switch 46, it is contemplated that other activation schemes could be used. For example, a one-time use pull tab could be used to activate the battery's electrical conduction to the circuit, once removed by the user at the time of patch activation. Finally, it is contemplated that the switch 46 could provide additional functionality after patch activation. For example, pressing the switch 46 a second time after patch activation, or pressing the switch in a pre-selected pattern, or pressing the switch for a predetermined amount of time, could cause the integrated circuit 38 to take a particular action. Such additional functionality could include any or all of reinitializing the integrated circuit 38, reinitializing the communications chip or temperature sensor, placing the integrated circuit 38 back into a sleep mode, obtaining a battery life reading, changing the speed of data collection (faster or slower), changing a mode of operation of the integrated circuit 38 (e.g., test mode, diagnostic mode, send/receive mode), etc.

Figure 4:
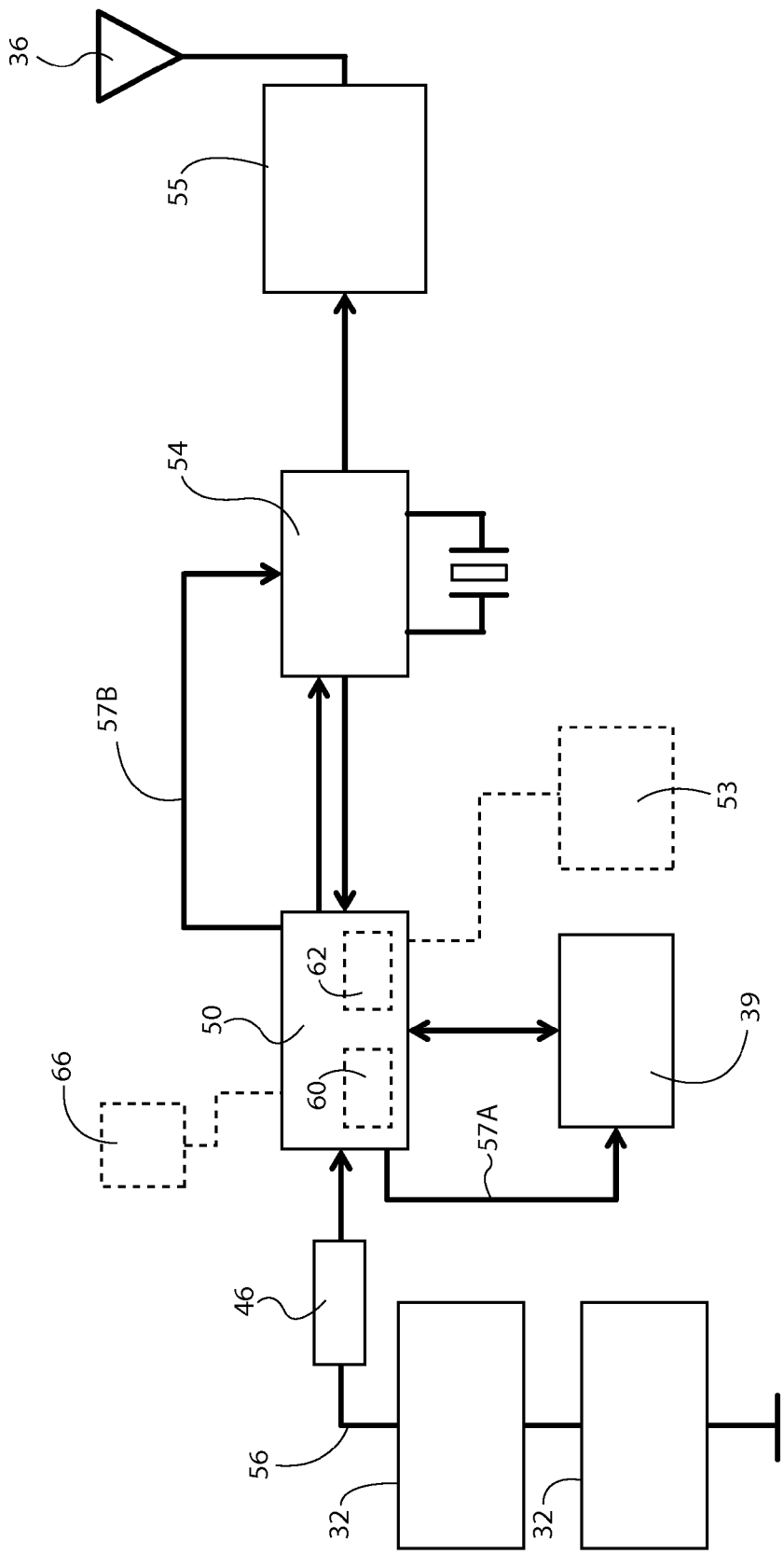
FIG. 4 illustrates a top schematic view of an example electronic circuit of the example patch.

Turning now to FIG. 4, one example integrated circuit 38 will be described in greater detail. Although illustrated as a multi-chip solution, it is contemplated that more or less chips can be used, such as a single-chip solution. Further, although different example microchips are discussed herein, it is understood that various other microchips capable of sensing, processing, powering, communicating, etc. can also be used. As shown in FIG. 4, a multi-chip solution can generally include a microprocessor 50, a temperature sensor 39 chip, and a communications chip 54. These chips could be separate, or could be combined together (for example, the microprocessor 50 could be combined with the communications chip 54 and/or the temperature sensor 39). In the shown example, the temperature sensor 39 is a separate element at is located at one end of the patch 10, while the microprocessor 50 is located at another end of the patch. It is contemplated that the communications chip 54 is electrically connected to the antenna 36, and can include one or more of the communication protocols discussed herein, including Bluetooth, Bluetooth low energy, NFC, RFID, Wifi, Cellular (analog or digital, including all past or present iterations), ZigBee, RuBee, etc. It is further contemplated that the communications chip 54 can be used in an antenna matching network layout 55 to make the impedance of the antenna 36 to be relatively close to the impedance of the radio module.

In one example, the microprocessor 50 can be a programmable microprocessor that can include various features and capabilities. The microprocessor 50 includes a programmable computing core that is capable of any or all of processing commands, making calculations, tracking/reading data, storing data, analyzing data, adjusting/manipulating data, receiving new commands or instructions, etc. The microprocessor 50 is capable of operating the temperature sensor 39 chip (and any optional auxiliary temperature sensors 53) at predetermined or variable temperature read intervals, operating a timer 60, and storing the temperature and time-logged datapoints in an on-board memory 62 and/or even in an auxiliary memory storage device, transferring the temperature and time-logged datapoints between the different memory devices, outputting commands and/or data to the computing device 14, and transmitting temperature data stored since the time of the last connection to the computing device 14. If two-way communication were enabled, the microprocessor 50 could also receive commands and/or data from the computing device 14. Additionally, each time the computing device 14 is in proximity to the patch 10 (e.g., within the communication range of the communication protocol being utilized), the microprocessor 50 should transfer updated data (and also historical data) to the computing device 14.

Various transmission schemes can be used to transmit current temperature data, as well as historical temperature data. With the use of Bluetooth, and especially Bluetooth low energy, it may not be possible to transmit the entire historical dataset to the computing device 14 in a single transmission. Thus, the microprocessor 50 may be configured to transmit the historical data in discrete packages that are assembled by the computing device 14 over time. Preferably, the patch 10 will transmit a combination of current data and historical data so that a complete picture of the measured temperature over time can be obtained by the computing device 14, even if it is out of range of the patch for some time. In one example embodiment, the patch 10 could transmit, in each transmission unit, the instant temperature data and a portion of the historical temperature data. Both instant and historical temperature data can include a unique numerical identifier or time stamp, together with the temperature data, such as: [00001, 98.6 degrees]. The unique numerical identifier or time stamp can enable the software application to properly assemble the data into a temperature-time chart to illustrate a history of the temperatures recorded by the patch 10. In this manner, the software application will always display the current patient temperature, as well as some or all of the historical data. For example, the computing device 14 may need to receive multiple transmissions over a few minutes from the patch 10 before a complete historical temperature dataset is obtained. However, this scheme can be beneficial in that it permits the patch 10 to function within the boundaries of Bluetooth low energy data transmission, as well as ensure that the computing device 14 can obtain a complete historical dataset even if the patch 10 is out of range for a period of time. Still, the patch 10 may only transmit current temperature data and could rely upon the software application 300 to assemble the data. If the computing device 14 is in constant proximity with the patch 10, updated data can be sent periodically per a predetermined time interval (e.g., every 5 seconds, every 10 seconds, every minute, etc.) or an adjustable time interval (e.g., adjustable manually or automatically via the software application, if two-way communication is enabled).

In other examples, the microprocessor 50 could include error checking and control functionality to ensure data integrity of the measured temperatures. The error checking and control functionality can operate with respect to various data flowing into or out of the microprocessor 50, including temperature-read data, data stored in and/or read out of memory, and/or data transmitted into and/or out of the patch 10. It is contemplated that the wireless communication subsystem will also include error checking and control functionality, and the microprocessor 50 can work together with or independent of such communication subsystems.

The microprocessor 50 can further include an electrical connection 56 to the flexible battery 32, and may selectively distribute electrical power to either or both of the temperature sensor 39 chip and communications chip 54 via power lines 57A, 57B. The microprocessor 50 can include any or all of a voltage regulator or modifier (which may or may not include a coil), such as a voltage upconverter or downconverter, a power conditioner, and/or one or more capacitor(s) to stabilize voltage and power flow. In one example, the temperature sensor chip 39 can operate at about 3 volts DC (VDC), while the single flexible battery 32 provides only about 1.5 volts DC. Thus, a 3 VDC (or greater) battery could be utilized (including two or more 1.5 VDC batteries 32 arranged in series, as shown). However, where only a single battery 32 is used, it is contemplated that the microprocessor 50 can upconvert the 1.5 VDC of the battery 32 via the voltage regulator or modifier to selectively provide 3 VDC to the temperature sensor chip 39 when operation of the temperature sensor chip 39 is desired. When the temperature sensor chip 39 is not operating, the microprocessor 50 may discontinue supplying power to the temperature sensor chip 39 to conserve power. Still, it is contemplated that a voltage regulator or modifier and/or capacitor could be separately provided apart from the microprocessor 50. Similarly, the microprocessor 50 can selectively provide power to the communications chip 54 for various reasons. Where an actively-powered communication protocol is used (e.g., Bluetooth, Bluetooth low energy, WiFi, Cellular, etc.), the microprocessor 50 may provide continuous or intermittent power to the communications chip 54 for operation thereof. It is contemplated that the microprocessor 50 can periodically discontinue supplying power to the communications chip 54 to conserve power. For example, if the temperature data is sent periodically, the microprocessor 50 may provide limited or even no power to the communications chip 54 during no data transmission intervals. Alternatively, where a passively-powered communication protocol is used (e.g., NFC or RFID), the microprocessor 50 may provide limited or even no power to the communications chip 54. Instead, the communications chip 54 could obtain all of its power from the NFC or RFID (or other) transmission. In addition, an optional auxiliary memory could possibly be passively powered by a NFC, RFID or other passive-power transmission system to enable data reading even if the battery 32 has been depleted. Still, if the communications chip 54 includes additional features, then the communications chip 54 may still receive some continuous or intermittent power from the microprocessor 50.

The microprocessor 50 can include additional features. For example, the microprocessor 50 includes a timer 60, which can be a real-time clock or other mechanism for tracking time. Thus, the microprocessor 50 is capable of associating each temperature reading from the temperature sensor 39 chip with a time stamp, such as a time stamp indicative of the real, local time that the temperature reading was taken. It is also contemplated that the timer 60 could track and report time based upon a standard time zone, and the software application could provide the adjustment into the user's local time zone. Alternatively, it is contemplated that the timer 60 may not track real time, but may instead track some time-associated data that can be interpreted, estimated, or translated by the software application as a real time stamp.

In a further example, the timer 60 may track real-time (e.g., elapsed time), but the microprocessor may associate each temperature reading from the temperature sensor 39 chip with a unique identifier, such as a unique numerical identifier. The microprocessor 50 may be programmed to obtain a temperature reading from the temperature sensor 39 every 5 seconds, for example, which is tracked by the timer 60. When the temperature reading is obtained, the microprocessor 50 tags it with a unique numerical identifier, which could be sequential, based on a pattern, random, etc. In one example, over a 30 second period with temperature readings taken every 5 seconds, the microprocessor 50 could tag the readings sequentially, such as: [00001, 98.6 degrees]; [00002, 98.7 degrees]; [00003, 98.7 degrees]; [00004, 98.8 degrees]; [00005, 98.7 degrees]; [00006, 98.6 degrees]. These readings are saved to the on-board memory 62, and are wirelessly transmitted to the computing device 14.

If two-way communication with the computing device 14 is enabled, the timer 60 or other portion of the microprocessor 50 could accept a timer initialization command from the computing device 14 and associated software application to start operation of the timer 60 whenever the user begins to use the patch 10, which is otherwise generally in an inactive or very low power state during storage. The timer initialization command can start operation of the timer 60, and can also provide an accurate, actual start time (or time-associated data) so that the timer 60 can begin to accurately report and log the time stamps of each temperature read. In addition or alternatively, the timer 60 could be configured to accept one or more timer adjustment signal(s) to periodically ensure the timer 60 is accurately keeping time.

The on-board non-transitory memory 62 of the microprocessor 50 is configured to store some or all of the temperature read data and associated time stamp or numerical identifier. It is contemplated that each temperature read from the temperature sensor 39 chip will have at least an associated time stamp or numerical identifier therewith, or other unique identifier, and each discrete temperature read will be stored in memory with its time stamp or numerical identifier. Each temperature read could also be stored together with additional data, such as a temperature read reference number, a patch 10 device unique ID (UID, which can be hard-coded into the microprocessor 50 or communications chip), a flag indicating whether or not each discrete temperature read datapoint has been wirelessly transmitted to the computing device 14, a flag indicating whether or not each discrete temperature read datapoint has been adjusted, modified, converted, etc., and/or various other pieces of data associated with each temperature read datapoint. The on-board memory 62 of the microprocessor 50 is preferably sufficient to retain a portion, such as some or even all, of the temperature datapoints read during the operational life of the patch 10 (e.g., generally governed by the usable life of the batteries 32). For example, the on-board memory 62 could retain every temperature datapoint read, regardless of whether or not the datapoints have been wirelessly transmitted to the computing device 14. During each wireless transmission, the software application could re-read a complete copy of the data, or only the most recent unread incremental datapoints.

Alternatively, the on-board memory 62 of the microprocessor 50 may only be sufficient to store a fixed amount of data that is less than all of the temperature datapoints. In one example, the on-board memory 62 may only be able to store 25% or 50% of the total temperature datapoints intended to be read during the operational life of the patch 10. Thus, the computing device 14, which generally has a much larger available memory space, may retain the complete temperature data read history of each patch 10, while the on-board memory 62 of the microprocessor 50 only retains a small fixed amount, such as the last 500 datapoints or the last few minute or hour's worth of datapoints, or other amount of data, etc. It is understood that various mechanisms could be used to accommodate the fixed amount of on-board memory 62. For example, when the memory is full the microprocessor 50 could continuously overwrite the oldest memory register such that the most recent temperature readings are always available to be read by the software application and computing device 14, or the microprocessor 50 could even stop storing temperature readings.

In addition or alternatively, the circuit 34 could include an auxiliary memory storage device that preferably is of sufficient size to record all anticipated temperature read datapoints. In one example, the auxiliary memory storage device could be a separate chip, or could be incorporated as part of another chip, such as part of the communications chip 54. In one example, the auxiliary memory storage device could have 64 kilobytes of memory (or more, or less) capable of storing approximately 100,000 datapoints, although more or less memory (in one or more storage devices) is contemplated. Thus, some or all of the temperature read datapoints stored in the on-board memory 62 of the microprocessor 50 can be transferred to the relatively larger auxiliary storage device for long-term storage. The transfer of such datapoints can be performed according to various schedules, on-demand, etc. For example, the transfer of some or all datapoints from the on-board memory 62 to the larger auxiliary storage device can be performed at pre-set time intervals, such as every 30 seconds, every minute, every five minutes, etc. In another example, transfer of some or all datapoints from the on-board memory 62 to the auxiliary storage device can be performed once the on-board memory 62 has reached a predetermined capacity, such as 50% full, 75% full, 90% full, or 100% full, etc. In yet another example, transfer of datapoints from the on-board memory 62 to the auxiliary storage device can be performed on a rolling basis. For example, datapoints initially written to the on-board memory 62 can then be sequentially transferred to the auxiliary storage device, or once the on-board memory 62 is full, the oldest datapoint can be transferred to the auxiliary storage device to make room for the next newest datapoint to be written to the on-board memory 62. It is also contemplated that data can be transferred back from the auxiliary storage device into the on-board memory 62, as desired. Finally, it is contemplated that either or both of the on-board memory 62 and auxiliary storage device can include volatile or non-volatile memory that may or may not need a continuous power supply.

The temperature sensor 39 chip can utilize various types of sensors or techniques to determine the temperature of the patient, such as on-chip PN junction sensor. For on-body temperature readings, the temperature sensor 39 chip would be highly accurate within the typical human body temperature range of 35-43 degrees Celsius (e.g., 95-110 degrees Fahrenheit). Preferably, the temperature sensor will have a high accuracy, such as +/−0.5 degrees Celsius, more preferably +/−0.25 degrees Celsius, or even more preferably +/−0.1 degrees Celsius. Still, various other types of internal and/or external temperature sensors could be utilized, such as thermistors and resistance temperature detectors (RTD).

Thus, the temperature sensor 39 chip can sense the body temperature of the user through the skin-contact adhesive 40. It is contemplated that the foam material of the adhesive 40 could provide an insulation barrier around the temperature sensor 39 that could mitigate outside influences. Turning back to FIG. 3 briefly, the adhesive 40 could include a hole 41 extending therethrough that is aligned with the location of the temperature sensor 39. The hole 41 can provide an unobstructed path between the patient's skin and the temperature sensor 39. In one example, the temperature sensor 39 could extend partially through the hole 41 to be spaced a distance from the patient and obtain temperature readings by sensing the radiated heat from the patient's skin. In addition or alternatively, the temperature sensor 39 could extend partially or completely through the hole 41 to be in direct contact with the patient's skin to obtain a more direct temperature reading. In yet another embodiment, a spacer, such as the previously-described hydrogel, could be disposed between the patient's skin and the temperature sensor 39 to provide a thermally conductive path.

In addition or alternatively, the temperature sensor 39 could further be provided with additional features to enhance the ability to quickly and accurately sense the patient's skin temperature. For example, a reflector could be disposed about the temperature sensor 39 to concentrate the radiated heat from the patient's skin more directly onto the temperature sensor 39. In one example, the reflector could be located vertically above the temperature sensor 39 (when viewed in the normal operating condition of the patch 10), such as located between the upper flexible single sided adhesive 20 layer and the temperature sensor 39. The reflector could even be incorporated at part of the adhesive 20 layer, or the substrate 37, or even as part of the temperature sensor 39 itself. The reflector could have various shapes and sizes, and could include various materials, such as a metallized layer or a metal foil layer. Because the antenna 36 is located at the opposite end of the patch 10 from the temperature sensor 39, the reflector should have little or no impact upon the strength of the transmitted radio signal. In addition or alternatively, it is contemplated the upper adhesive 20 layer could act as an insulating layer to provide insulation from the temperature sensor to the ambient surroundings to thereby help with temperature accuracy.

It is contemplated that the temperature sensor 39 can sense the temperature of the user directly, or may even interpolate/estimate the temperature indirectly based upon a predetermined algorithm or the like. Moreover, it is contemplated that the patch 10 can utilize a predetermined algorithm or the like to provide an indication of the core body temperature of the user based upon the skin surface temperature measurements. It is generally accepted that the axillary (i.e., underarm) temperature is slightly different than a body's core temperature, and therefor the microprocessor 50 (or even the software application of the computing device 14) can provide a suitable adjustment to the temperature data. The microprocessor 50 can obtain temperature datapoints from the temperature sensor 39 periodically per a predetermined time interval (e.g., every 1 second, every 3 seconds, every 5 seconds, every 6 seconds, every 10 seconds, every 30 seconds, every minute, etc.) or an adjustable time interval. In one example, the microprocessor 50 can obtain temperature datapoints at a fixed time interval during the operational lifetime of the patch 10. In another example, the microprocessor 50 can obtain temperature datapoints at variable time intervals, which could be dynamically adjusted by the microprocessor 50 or software application, or even by the user. In yet another example, the microprocessor 50 could obtain temperature datapoints at different rates depending upon particular variables, such as operational time of the patch 10. For example, the microprocessor 50 could obtain temperature datapoints at a relatively fast interval (e.g., 1 read per second or per 5 seconds) during the first 5-10 minutes of operation so that the user can have relatively quick and instant feedback of the patient's temperature. Thereafter, the temperature read interval could be reduced to 1 read per 30 seconds or per minute) to conserve battery power or memory. If two-way communication is enabled, the software application could provide a "boost" mode to re-enable the fast data collection scheme on-demand if desired. Alternatively, the data sensing interval could be based on the battery life (e.g., obtaining less data reads when the battery is drained below a threshold amount), memory capacity (e.g., obtaining less data reads when the available memory capacity is below a threshold amount), or even temperature sensed by the temperature sensor 39 (e.g., slower data reads when the sensed temperature is in a predetermined normal range, and faster data reads when the sensed temperature exceeds a predetermined elevated or reduced range).

In addition or alternatively, the patch 10 can include one or more auxiliary sensors to measure, for example, multiple body temperatures or even ambient environmental conditions around the user. The one or more auxiliary sensors 53 could be electrically coupled to the temperature sensor 39 chip via optional external connections, or could even be built-in. The patch 10 could utilize these auxiliary sensors to dynamically adjust the temperature readings of the user and/or alerts of the software application based upon ambient conditions. For example, if the user is located in a very hot climate, it might be expected for the user to have a slightly higher body temperature than a user in a very cold climate. The software application could dynamically adjust a high-temperature alarm to accommodate such environmental variables. It is further contemplated that the auxiliary sensor 53 could also include various other sensors, such as ambient humidity, ambient pressure, ambient light, sound, and/or radiation levels, patient bodily functions, time, patient movement (e.g., via an accelerometer), patient pulse, blood-oxygen levels, EKG, etc., and the software application could dynamically adjust alarms or the like based upon one or a combination of various variable readings. Finally, it is preferred that the temperature sensor 39 (and the circuit 34 overall) will not be exposed to a high temperature during the assembly process, and as such the temperature sensor 39 chip can be calibrated at the factory. However, it is contemplated that the temperature sensor 39 chip can be self-calibrating, and/or could be calibrated by the microprocessor 50 and/or computing device 14.

Finally, the microprocessor 50 can include various additional optional features. In one example, the microprocessor 50 can include one or more output devices 66 to provide feedback to the user, such as indicators, alarms, etc. The output devices 66 could include any or all of visual (e.g., LED lights, displays, etc.), audible (e.g., speakers, etc.), or tactile (e.g., vibration, etc.). In one example, one or more optional LED lights (or other type of lights, displays, etc.) could be used to indicate that the user of the patch 10 has either a low, normal, or high temperature. The LED lights could be illuminated yellow for a low temperature, green for a normal temperature, or red to indicate a high temperature, or could provide these indications via changing flashing intervals. In another example, the LED lights could be used to dynamically (e.g., via color change, flashing intervals, etc.) to indicate battery status and/or actual or estimated time left for operation of the patch 10. In yet another example, the LED lights could be used to indicate an operational status of the patch 10, such as on/off, proper/faulty operation, successful or failed connection with the computing device 14, active communication with the computing device, etc. Similar functions could be used with an audible or tactile output device. The microprocessor 50 can be connected to any or all of the temperature sensor 39, communications chip 54, or other components in various manners, such as a two wire interface or the like.

As described herein, the patch 10 is an active device with an on-board power source. In the shown embodiment, the use of the Bluetooth communications system means that the device is a fully active device using the on-board power source. For example, the electronics inlay 30 can include one or more thin, flexible batteries 32. The flexible batteries 32 can be provided in various capacities, such as a 5 mAh, 10 mAh, 15 mAh, or other capacity, etc. Although one battery is described in detail below, it is understood that all batteries used in the patch 10 could be the same or even different. Even through in some embodiments the wireless communication may be partially or entirely powered by the wireless signal itself (e.g., NFC communication protocols), any or all of the onboard microprocessor, timer, memory and/or temperature sensor may be actively powered. In an effort to make the patch small, thin, lightweight and flexible, a thin printed battery can be provided as the onboard power source. Various methods can be used to manufacture flat batteries. In one example, the electrochemical cells (i.e., batteries) are typically printed and/or laminated on a continuous, flexible substrate web, and may be formed into a roll or the like. The individual batteries can be removed from the roll, such as one at a time. For example, the batteries can be cut from the roll, and/or perforations of the flexible substrate roll can be provided for easy tear off. In addition, the batteries can further be manufactured in an integrated process with one or more electrical components, such as an antenna, display, and/or a processor, for example. The multiple facets of this application could be used in the total package described and/or they could be used individually or in any combination.

As used herein, unless otherwise explicitly indicated, all percentages are percentages by weight. Also, as used herein, when a range such as "5-25" (or "about 5-25") is given, this means, for at least one embodiment, at least about 5 and, separately and independently, not more than about 25, and unless otherwise indicated, ranges are not to be strictly construed, but are given as acceptable examples. Also herein, a parenthetical range following a listed or preferred value indicates a broader range for that value according to additional embodiments of the application.

One method of mass-producing such cells includes depositing aqueous and/or non-aqueous solvent inks and/or other coatings in a pattern on a special substrate, such as a laminated polymeric film layer, for example. The depositing can be by means of, for example, printing electrochemical inks and/or laminating a metallic foil, such as zinc foil, for example, on one or more high-speed web rotary screen printing presses, especially if the desired volumes are very high. If volumes are relatively lower, say in the quantities of only about several million or less, then relatively slower methods such as web printing with flat bed screens could be appropriate. If the volumes are even lower, such as hundreds or thousands, then a sheet-fed flat bed printing press may be utilized, for example. Still, various printing methods can be used for various desired quantities.

After the inks are printed and/or the solids have been properly placed, the cells can be completed (e.g., sealed, die cut, stacked and/or perforated and wound into a roll, or stacked if sheets are used on a printing press). This cell manufacturing process can also be utilized for integrating one or more individual cells with an actual electronic application, or into batteries comprising multiple cells connected in series or parallel, or some combination of the two. Examples of such devices and corresponding processes will be described later, but many additional embodiments are also contemplated.

As discussed above, the battery may be described as a printed, flexible, and thin. Such a cell/battery can include, for example, a lower film substrate that can utilize a special polymer laminate that has special features, possibly including, for example, a high moisture barrier layer in the center that is surrounded by polymer films on both sides. Furthermore, one or both outside surfaces can be made to be print receptive for printing information, logos, instructions, identifications, serial numbers, graphics, or other information or images, as desired.

Depending on which construction of this battery is used, one ply of a multi-ply substrate could also feature a heat-sealing layer that might be co-extruded adjacent the barrier coating. In addition, a portion one substrate layer of a cell of at least some embodiments could utilize a cathode current collector and/or an anode current collector, such as carbon, for example, printed or coated or otherwise applied on a portion of the film substrate. At an outside contact area of this collector can also be printed a layer of a relatively highly conductive ink, such as carbon, gold, silver, nickel, zinc, or tin, for example, to improve the conductivity to the application connection, if desired. However, if the battery application is used for relatively low current requirements, then the higher conductive layer contact material, or even the current collector, may not be utilized for one or both electrodes.

For at least some embodiments, a water-based ink electrochemical layer is printed as the cathode. Such a cathode layer can include, for example, manganese dioxide ($MnO_2$), carbon (e.g., graphite), a polymer binder, and water. Other formulations for the cathode layer can also be utilized with or without any of these materials. If a cathode collector layer is used, the cathode electrochemical layer will be printed on at least a portion of the cathode current collector, which is printed or otherwise applied first to the substrate. Still, the cathode current collector may or may not form a portion of the cathode layer.

Regarding the anode, in an off-line operation, a dry-film adhesive layer, possibly using a release liner, can be applied to the zinc foil. The zinc foil can then be laminated to the base substrate. Additionally, the anode layer could be applied by printing a zinc ink onto the substrate or on top of a collector, such as carbon. Where carbon is used, it could be printed in the same station as the carbon collector used for the cathode and electrical bridge.

Optionally, printed over one or both the anode and cathode, is a starch ink or similar material. The starch ink can act as an electrolyte absorber to keep the electrodes "wet" after an aqueous electrolyte solution is added to the cell. This starch ink could also include the electrolyte salts and the water used for the cell reaction. A paper layer over the anode and cathode could be used in place of the printed starch. In at least one embodiment, the construction of the printed starch layer with the addition of the aqueous electrolyte could be replaced, for example, by a printable viscous liquid (which could include a gel, or some other viscous material) that effectively covers at least a portion, such as substantially all, of each electrode. One such printable gel is described in United States Patent Publication 2003/10165744A1, published on Sep. 4, 2003, and incorporated herein by reference. These viscous formulations could, for example, utilize the electrolyte formulas and concentrations as discussed herein.

Optionally, for some embodiments, after the two electrodes are in place, with or without the starch layer(s), an optional cell "picture frame" can be added. This could be done using a number of different methods. One method is to print this optional cell picture frame with a dielectric ink and/or adhesive, for example. Another method is to utilize an optional polymer sheet or a laminated polymer sheet that includes adhesive layers, that is stamped, die cut, laser cut or similar methods to form the appropriate "pockets" (inner space or spaces) to house materials of each unit cell as well as to expose the electrical contacts to connect the device. It is contemplated that the flexible battery can be formed with or without the frame. For example, while the frame can offer one method for providing inner space for the electrochemical cells, it is also contemplated that the first and second substrates could be secured together to provide the inner space for the electrochemical cells without the use of a frame.

To ensure good sealing of the picture frame to the substrates, and to provide good sealing of the contact feed-through (providing an electrical pathway from the cell inside to the cell exterior), a sealing or caulking adhesive could be printed over the contact feed-through and the substrate, such as in the same pattern as the cell frame, for example, prior to the frame being printed or prior to the polymer sheets being inserted, for example.

This sealing or caulking material could be pressure sensitive, and/or heat sensitive, or any other type of material that would facilitate sealing to both surfaces.

After the dielectric picture frame is printed and dried and/or cured, a heat sensitive sealing adhesive can be printed on top of the frame to allow good sealing of the top substrate to the cell frame. This cell picture frame could also comprise a polymer film or a laminated film of about 0.015" thick (range of about 0.003"-0.050") that is pre-punched and then laminated in registration to match the preprinted caulking adhesive layer described above.

Zinc chloride ($ZnCl_2$) can be chosen as the electrolyte, for at least some embodiments, in the concentration range of about 18%-45% by weight, for example. In one example, about 27% may be preferred. The electrolyte can be added, for example, to the open cell. To facilitate processing on the line, this electrolyte, or a different electrolyte, could be thickened with, for example, CMC at about a level of about 0.6 wgt % (range of about 0.05%-1.0%).

Other useful electrolyte formulations, such as ammonium chloride ($NH_4Cl$), mixtures of zinc chloride ($ZnCl_2$) and ammonium chloride ($NH_4Cl$), zinc acetate ($Zn(C_2H_2O_2)$), zinc bromide ($ZnBr_2$), zinc fluoride ($ZnF_2$), zinc tartrate ($ZnC_4H_4O_6.H_2O$), zinc per-chlorate $Zn(ClO_4)_2.6H_2O$), potassium hydroxide, sodium hydroxide, or organics, for example, could also be used.

Zinc chloride may be the electrolyte of choice, providing excellent electrical performance for ordinary environmental conditions normally encountered. Likewise, any of the above mentioned alternative electrolytes, among others, could be used in concentrations (by weight), for example, within the range of about 18%-50%, with the range of about 25%-45% used for at least some other embodiments. Such compositions could also provide acceptable performance under ordinary environmental conditions. When zinc acetate is used to achieve improved low temperature performance for low temperature applications, the zinc acetate concentration in the range of about 31-33, is often acceptable, although ranges of about 30-34, about 28-36, about 26-38, and even about 25-40, weight percent, could also be utilized.

The use of electrolytes other than of zinc chloride can provide improved cell/battery electrical performance under some differing environmental conditions. For example, about 32% by weight zinc acetate (F.P.—freezing point—about 28° C.) exhibits a lower freezing point than about 32% by weight zinc chloride (F.P. about −23° C.). Both of these solutions exhibit a lower freezing point than of about 27% zinc chloride (F.P. about −18° C.). Other zinc acetate concentrations, e.g. about 18-45 or about 25-35 weight percent, also exhibit reduced freezing points. Alternatively, an alkaline electrolyte such as Sodium hydroxide (NaOH) or potassium hydroxide (KOH) could be used as an electrolyte to provide improved cell/battery electrical performance under some differing environmental conditions. The cell performance could be greatly enhanced due to the much higher conductivity of the KOH electrolyte. For example, a good working range of KOH would be concentrations (by weight) within the range of about 23%-45%.

Use of such electrolyte formulations as substitutes for zinc chloride, or in various mixtures used in cells, can allow for improved performance at low temperatures. For example, it has been found that the use of an about 32% zinc acetate electrolyte substantially improves low temperature (i.e. below about −20° C.) performance of a voltaic cell. This type of electrochemical cell performance improvement at low temperature can be utilized in the growing business of battery assisted RFID tags, for example, and/or other transient (transportable) electrically operated devices, such as smart active labels and temperature tags, for example, which may be used in cold environments.

For example, many products that are shipped today, such as food products pharmaceuticals, blood, etc, may require low temperature storage and shipping conditions, or even low temperature operation. To ensure safe shipment of such goods, these items can be tracked with RFID tags, sensors, and/or displays. These tags and/or labels might require electrochemical cells and/or batteries to operate effectively at temperatures at, or even below, −20° C., such as at about −23° C., about −27° C., or even at about −30° C. or less.

The upper substrate of a cell package could utilize a special laminated polymeric film. The upper layer is sealed around the edges of the cell frame by means of a pressure sensitive adhesive (PSA), and/or with the heat sensitive sealing adhesive that was previously printed or just with the heat sealing layer of both the upper and lower substrates, thus confining the internal components within the cell frame.

The above-described constructions can be wet cell constructions; however, using a similar cell construction, the battery could be also be made into a reserve cell construction, which has the benefit of providing extended shelf life prior to the application of a liquid. The printable, flexible, zinc chloride thin cell is made environmentally friendly.

The devices for which this technology can be used are extensive. Devices that utilize relatively low power or a limited life of one to three years, and possibly longer, could function utilizing a thin cell/battery of the type described herein. The cell, as explained in the above paragraphs and below, can often be inexpensively mass-produced so that it can be used in a disposable product, for example. The low cost allows for applications that previously were not cost effective, and could now be commercially feasible.

The electrochemical cell/battery according to the application might have one or more of the following advantages:
Flat, and of relatively uniform thickness, where the edges are thinner than the thickness at the center;
Relatively thin;
Flat, and of relatively uniform thickness, where the edges are of about the same thickness as the center;
Flexible;
Many geometric shapes are possible;
Sealed container;
Simple construction;
Designed for high speed and high volume production;
Low cost;
Reliable performance at many temperatures;
Good low temperature performance;
Disposable and environmentally friendly;
Both cell/battery contacts provided on opposite surfaces, or even the same surface;
Both Cell/battery contacts can be provided at many locations on the battery exterior;
Ease of assembly into an application; and
Capable of being easily integrated in a continuous process at the same time that the electronic application is being made.

The above provides a general description of various cell constructions according to some embodiments of this application, and further details utilizing drawings follow below. Cell and battery production processes for cell manufacturing, printing and/or assembly also will be described as well.

In one example, such as where relatively high speed, high output manufacturing is contemplated, such as 50 linear feet per minute or another relatively high speed, multiple webs can be used. It is to be understood that the multiple webs can be generally continuous, and can be utilized with known web manufacturing equipment. A first web can be relatively thin, such as ~0.001"-0.010" and preferably about 0.002-0.006", flexible base substrate including a multi-ply laminated structure or single ply material. In one example, the multi-ply structure can include five layers. Alternatively, the single ply material can include various materials, such as Kapton, polyolifins or polyester. Additionally, if the 0.001" layer is too thin to handle efficiently on the printing press and/or on other operations, then a thicker throw away support layer with a low tact pressure sensitive adhesive layer could be laminated to the thin substrate layer. Also, this 0.001" substrate layer could be made from more than one ply with a very thin oxide layer which performs as a water barrier on the inside surfaces. After the printing and assembly operations are completed, then the throw away support layer could be removed.

A second web could be a relatively thicker laminated structure including a PVC or Polyester film that is about 0.003-0.030" thick, and preferably about 0.006-0.015" thick. The second web can have a layer of pressure sensitive adhesive (without the release liner) at about 1-5 mils thick on one or both sides. After this laminated structure of the second web is completed, it can be applied to the first web. In addition or alternatively, the second web can be pattern cut using any type of mechanical means to allow for cavities for the cells active materials as well as an optional cavity for the cell/battery contacts. A third web can be a relatively thin laminated structure the same and/or similar to the first web. The completed three web structure may have a pressure sensitive adhesive on either side to allow the individual device assembly to be applied as a label. The cell/battery may be of the thin cell type, such as described in co-pending U.S. application Ser. No. 11/110,202 filed on Apr. 20, 2005 now issued U.S. Pat. No. 8,722,235, Ser. No. 11/379,816 filed on Apr. 24, 2006 now issued U.S. Pat. No. 8,722,233, Ser. No. 12/809,844 filed on Jun. 21, 2010 now issued U.S. Pat. No. 8,574,754, Ser. No. 13/075,620 filed on Mar. 30, 2011 (Abandoned), Ser. No. 13/625,366 filed on Sep. 24, 2012, and Ser. No. 13/899,291 filed on May 21, 2013 now issued U.S. Pat. No. 8,765,284, as well as issued U.S. Pat. Nos. 8,029,927, 8,268,475, 8,441,411, all of which are incorporated herein by reference.

Depending on the cell construction, the cell application, and/or the cell environment, it may be advantageous to have different barrier properties for the substrate. Due to the wide range of available vapor transmission rates available, the barrier layer can be chosen for each specific application and construction, as desired. In some cases, for example where the cell by design has a higher gassing rate and/or a short life, it may be appropriate and desirable to use a film with a higher transmission rate to allow for a larger amount of gas to escape, so as to minimize cell bulging. The barrier layer is designed to minimize water loss but still allow generated gasses of normal electrochemical reactions to escape thus reducing the chances if the thin cell to bulge. Another example would be an application that has a long shelf life or is in a hot dry environment such as a desert. In such cases, it may be desirable to have a barrier film with low transmission rates to prevent excessive moisture loss from the cell. At least one of the first and second substrate layers can comprise a plurality of laminated layers including an oxide barrier layer having a gas transmission rate that permits gas to escape through said plurality of laminated layers of said first or second substrate layer, but still reduces (e.g., minimizes) the escape of water vapor.

Various embodiments of example constructions of the laminated film substrates can be utilized. The lower and upper laminated film layers can, in most cases and for most applications, be of the same materials. In at least one embodiment, these film layers can be comprised of a five-ply laminate film, for example. In another example, the laminated film substrates can have four layers. The top layer placed on the inside of the cell has an example thickness of about 0.48 mil thick (about 0.2-5.0 mil) and is a high moisture barrier polymer layer film that provides a flexible, heat-sealable web that has the following barrier properties: oxygen transmission rate of less than about 0.045 cubic centimeters per 100 square inches per 24 hours at about 30 C and 70% relative humidity; and MVTR of between about 0.006-0.300 grams water per 100 square inches per 24 hours at about 40 C and 90% relative humidity.

Typically, this polyester film has an oxide or metalized coating on the inside of the laminated structure. These polymer (polyester)-based barrier films, which can have varying moisture transmission values depending on the type and the amount of vacuum deposited oxides, or metals, and can be laminated to the bottom polyester layer and which acts as a structural layer with a Urethane adhesive. The inside layer of these substrates can include a heat sealing layer. Another alternative high moisture barrier could be a flexible, heat-sealable web that has the following barrier properties: oxygen transmission rate of less than about 0.045 cubic centimeters per 100 square inches per 24 hours at about 73 F and 50% relative humidity; and MVTR of less than about 0.30 grams water per 100 square inches per 24 hours at about 100 F and 90% relative humidity.

In another example, an outside layer (or structural layer) of a multi-layer structure can include an about 2.0 mil (about 0.5-10.0 mil) layer of orientated polyester (OPET), which is laminated to the other layers by means of an urethane adhesive that is about 0.1 mil thick, for example. This "structural layer" can be a polyester orientated (OPET) film, or a polyester based synthetic paper, which is designated as a white micro-voided orientated polyester (WMVOPET).

The use of a thicker substrate, by increasing any or all of the polymer thicknesses, may have some advantages: These may include one or both of the following: The cells process better on printing press due to the thicker substrate being less temperature sensitive; and The cell package is stiffer and stronger.

In addition to the above specifications, either or both the outside and the inside layers could include the addition of a print-receptive surface for the required inks. The inside layer is used for the functional inks (such as the collector and/or electrochemical layers) while the outside layer can be used for graphical inks, if desired. Flat cell constructions having a sealed system might utilize a laminated structure that includes metallized films and/or a very thin metal foil or foils as a moisture barrier. Although such structures using a metal layer might have better moisture barrier properties than the constructions used for some of the above described embodiments, it might also have some disadvantages. These may include one or more of the following: Laminated structures with metal barriers (thin metal foil or a vacuum metallized layer) are likely more expensive; Laminated structures with metal layers have the possibility of causing internal shorts; and Laminated structures that include a metal barrier could interfere with the electronics of an application, such as the functionality of a RFID antenna, for example.

The film substrates can be comprised of numerous variations of polymeric film, with or without a barrier layer (including metal or other materials), and can utilize either mono-layer or multi-layer films, such as polyesters or polyolefin. Polyester is a good material to utilize because it provides improved strength permitting use of a thinner gauge film and is typically not easily stretched when used on a multi-station printing press. Vinyl, cellophane, and even paper can also be used as the film layers or as one or more of the layers in the laminated constructions. If a very long shelf life is desired, and/or the environmental conditions are extreme, the multi-ply laminate polymer could be modified to include a metallized layer such as obtained by vacuum deposition of aluminum in place of the oxide coating.

Alternately, a very thin aluminum foil could be laminated within the structure of the film layer, such as for layer, or in a different position. Such a modification could reduce already low water loss to practically nil. On the other hand, if the application is for a relatively short shelf life and/or a short operating life, a more expensive barrier layer could be replaced with a less efficient one which would be of a lower cost and still allow the cell to function for the required lifetime.

In applications where only an extremely short life is necessary, the cell package could instead use a film layer of a low cost polymer substrate such as polyester or polyolefin. It is possible that the pressure sensitive adhesive sealing system for adhering the frame to the top substrate and lower substrate could be replaced with a heat sealing system on the laminates.

In a simplified construction of the upper and/or lower laminate substrates, laminate barrier layers could be laminated together with urethane adhesive layer, for example. Alternatively, a substrate could be provided with an additional layer that is a barrier coating on barrier layer. In addition, layers could be laminated together with urethane adhesive layer.

Alternatively, an example seven-layer laminate substrate could be used for the substrate of the cell. A heat sealing layer can be laminated to the previous structure using an adhesive layer. The approximate 50-gauge heat seal layer can be a composite layer that also includes a heat sealing coating such as amorphous polyester (APET or PETG), semi crystalline polyester (CPET), polyvinyl chloride (PVC), or a polyolefin polymer etc. on polymer film such as polyester. This would thus make the top substrate and/or the bottom substrate of the previously described cell into a 7-ply construction. Depending on the thicknesses of the various layers, any of these structures (three-ply, four-ply, and seven-ply laminates, respectively), the total thickness of these laminates could be about 0.003" with a range of about 0.001-0.015" for at least some embodiments. Alternatively, different substrate constructions could be utilized as well, including more or less layers, depending on the desired applications and qualities.

The various conductive inks described herein could be based on many types of conductive materials such as carbon, silver, gold, nickel, silver coated copper, copper, silver chloride, zinc and/or mixtures of these. For example, one such material that shows useful properties in terms of conductivity and flexibility is silver ink. Furthermore, various circuits, electrical pathways, antennas, etc. that might be part of the printed circuitry can be made by etching aluminum, copper or similar type metallic foils that are laminated on a polymer, such as a polyester substrate. This could be done with many types (sizes and frequencies) of pathways and/or antennas whether they are etched or printed.

A thin printed flexible electrochemical cell includes a printed cathode deposited on a printed cathode collector (e.g., a highly conductive carbon cathode collector) with a printed or foil strip anode placed adjacent to the cathode. Electrochemical cells/batteries of this type are described in co-pending U.S. application Ser. No. 11/110,202 filed on Apr. 20, 2005 now issued U.S. Pat. No. 8,722,235, Ser. No. 11/379,816 filed on Apr. 24, 2006 now issued U.S. Pat. No. 8,722,233, Ser. No. 12/809,844 filed on Jun. 21, 2010 now issued U.S. Pat. No. 8,574,754, Ser. No. 13/075,620 filed on Mar. 30, 2011 (Abandoned), Ser. No. 13/625,366 filed on Sep. 24, 2012, and Ser. No. 13/899,291 filed on May 21, 2013 now issued U.S. Pat. No. 8,765,284, as well as issued U.S. Pat. Nos. 8,029,927, 8,268,475, 8,441,411, the disclosures of which is incorporated herein by reference. The electrochemical cell/battery can also include a viscous or gelled electrolyte that is dispensed onto a separator that covers all or part of the anode and cathode, and a top laminate can then be sealed onto the picture frame. This type of electrochemical cell was designed to be easily made by printing (e.g., through use of a printing press), and allows, for example, for the cell/battery to be directly integrated with an electronic application.

Turning now to FIGS. 5-8, a flexible battery for generating an electrical current is shown in various detail views. Though not explicitly stated, the flexible battery can include any of the battery structure or methodology described herein. The flexible battery, including one or more cells, is printed on a single side of a single substrate (the top substrate is not shown in FIG. 5 for clarity). It is understood that various portions of the battery could be printed on opposite sides of a substrate, although it can be more cost effective to print the battery on a single side of a substrate. Additionally, though the battery can be formed using a printing process for each element, some or all of the elements can be provided via a non-printed process, such as laminates, adhesives, strips of material, etc.

The battery includes a thin printed flexible electrochemical cell, which may include an optional sealed "picture frame" structure, that includes a printed cathode deposited on a printed cathode collector (e.g., a highly conductive carbon cathode collector) with a printed or foil strip anode placed adjacent to the cathode. The electrochemical cell/battery also includes a viscous or gelled electrolyte that is dispensed onto a separator that covers all or part of the anode and cathode, and a top laminate can then be sealed onto the picture frame. This type of electrochemical cell was designed to be easily made by printing (e.g., through use of a printing press), and allows, for example, for the cell/battery to be directly integrated with an electronic application.

Figure 5:
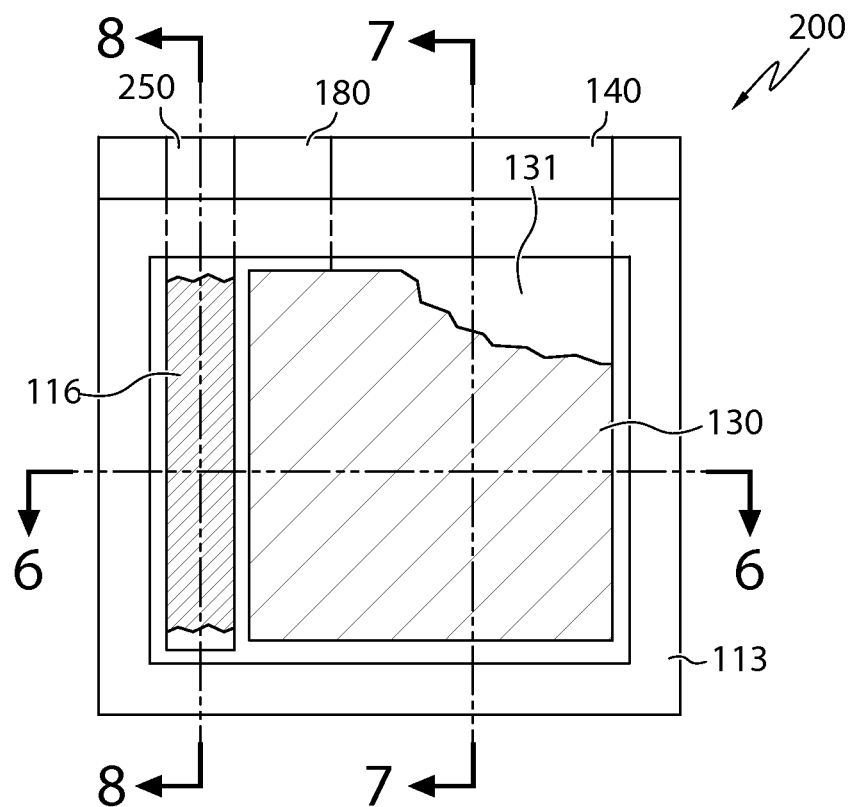
FIG. 5 illustrates a plan view of an example electrochemical cell.
Figure 6:
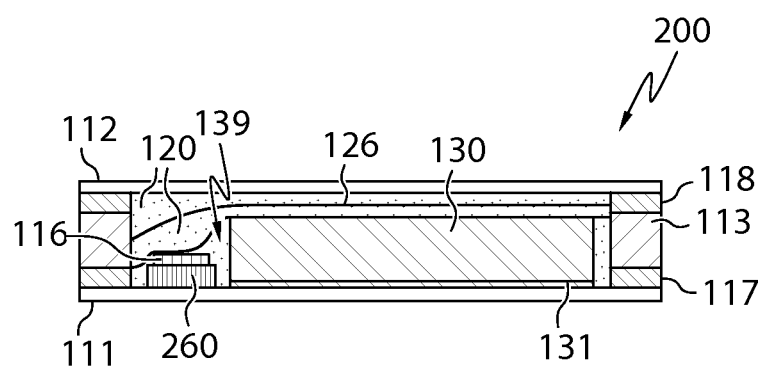
FIG. 6 illustrates a cross section view of the electrochemical cell taken through electrode areas along line 6-6 of FIG. 5.
Figure 7:
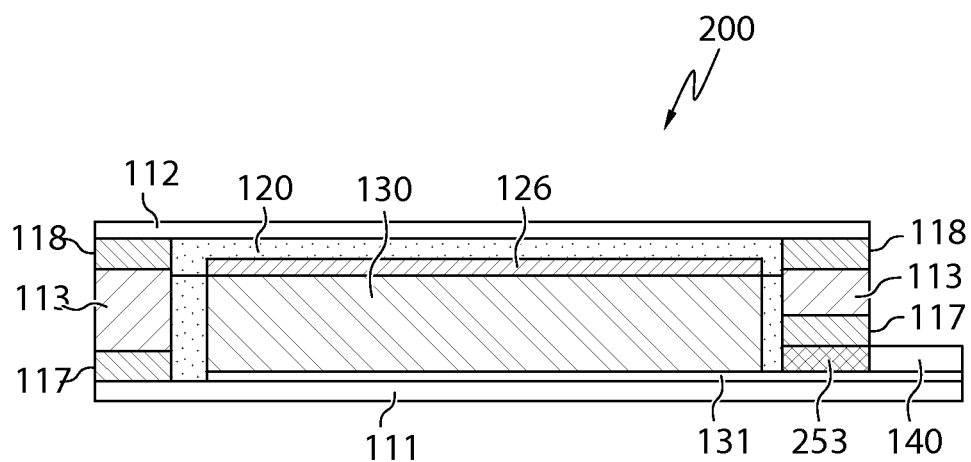
FIG. 7 illustrates a cross section view of the electrochemical cell taken through the entire length of the first electrode along line 7-7 of FIG. 5.
Figure 8:
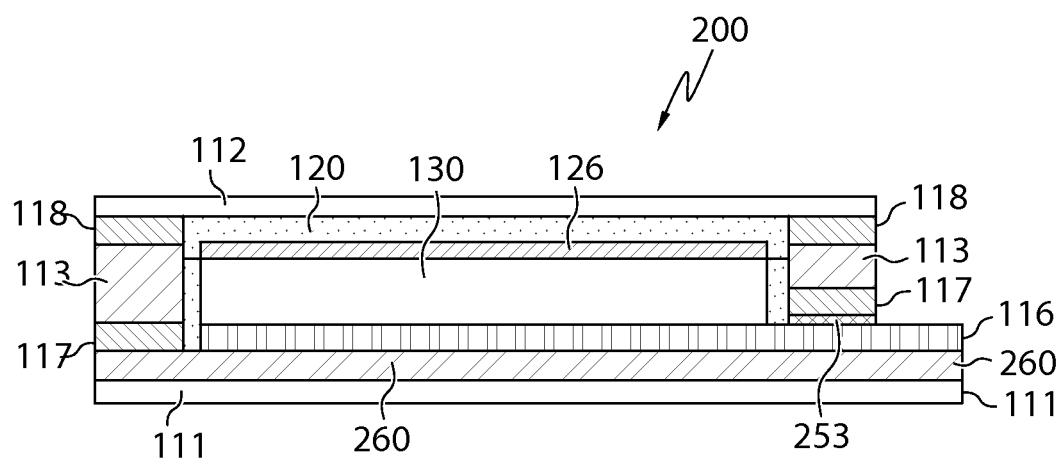
FIG. 8 illustrates a cross section view of the electrochemical cell taken through the entire length of the second electrode along line 8-8 of FIG. 5.

One flexible, printed battery 32 for use in the electronics inlay 30 herein is further described by FIGS. 5-8 which show an embodiment of a completed unit cell 200 in plan and sectional views. The cell 200 includes a top laminated film substrate (layer) 112, a lower laminated film substrate (layer) 111, and an extended area 180 that has positive contact 140 and negative contact 250. To provide greater clarity, cell 200 in FIG. 5 is shown without the top laminate 112, although it is shown in FIG. 6. The positive and negative contacts 140, 250 are exposed outside of the electrochemical cell for connection to the electronics inlay of the patch. Either or both of the positive and negative contacts 140, 250 may have a printed or laminated conductive layer thereon, such as a printed silver ink or the like, or may include other layer(s) that facilitate coupling or electrical conductivity to the electronics inlay. The positive and negative contacts 140, 250 may be the same as, or even different from, the battery contact pads 35A, 35B that are electrically coupled to corresponding battery electrodes 33A, 33B of the flexible circuit 34.

Additionally, the cell 200 includes a cathode layer 130 and an anode layer 116, each comprised of an electrochemical layer of a different composition that can interact through an electrolyte to create an electrical current. In various examples, the flexible battery can be manufactured (i.e., printed) directly or indirectly on the lower laminated substrate 111, or can even be separately manufactured (wholly or partially) and then attached directly or indirectly to the lower laminated substrate 111. In one embodiment, the lower laminated substrate 111 is a laminated film. The flexible battery further comprises a top laminate 112 being connected to said lower laminated substrate 111 and arranged in a covering relationship over the lower laminated substrate 111. The second top laminate 112 can also be a single or multi-layer laminated film. It is contemplated that the top laminate 112 could be used as the top layer of the battery, and/or that some or all elements of the electrochemical cell can be on or integrating the top laminate 112.

The lower and/or top laminated substrates 111, 112 can be a material that includes a plurality of laminated layers. The plurality of laminated layers can include a structural layer having an integrated barrier and/or a heat sealing layer, such as any described herein. The plurality of laminated layers can include any or all of an inner layer including a polymer film and/or a heat sealing coating, a high-moisture barrier layer, a first adhesive layer for connecting said inner layer to said high-moisture barrier layer, an outer structural layer including an orientated polyester, and/or a second adhesive layer for connecting said high-moisture barrier layer to said outer structural layer. The high-moisture barrier layer can include an oxide coated moisture barrier layer that non-hermetically seals the battery against moisture, and may not include a metal foil layer. The plurality of laminated layers could optionally include a metalized layer.

Additionally, a current collector layer can be provided underneath each of the cathode and anode of the electrochemical cell. The current collector layer can be provided via a dried or cured ink (e.g., printed), or can be provided via a non-printed process, such as laminates, adhesives, strips of material, etc. Indeed, all of the current collectors, anodes, and cathodes can be provided as cured or dried inks. Generally, the current collector layer is provided as a different material from the anodes and cathodes. Additional current collectors can be provided under the remaining cathode and anode. The anode and cathode of each cell can be printed, respectively, on each of the cathode collector and/or anode collectors. It is contemplated that any or all of the current collectors can be provided directly upon the lower laminated substrate 111, in the same printing station, although any or all of the current collectors could be provided on top of optional intermediate layers.

For example, prior to applying the cathode layer 130, a cathode collector 131 of highly conductive carbon is printed on the lower laminated substrate 111, any or all of which can be provided as layers. Optionally, a similar anode collector layer can also be provided underneath the anode. The anode and cathode of each unit cell can be printed in a co-planar arrangement. The anodes and cathodes can be comprised of cured or dried inks. In at least one embodiment, on the large area part of the cathode collector 131, the cathode layer 130 is printed using an ink comprising manganese dioxide, a conductor such as carbon (e.g., graphite) for example, a binder, and water. In various other examples, the cathodes can be printed using an ink that includes one or more of manganese dioxide, carbon, NiOOH, silver oxides Ag2O and/or AgO, HgO, oxygen O2 in the form of an air cell, and Vanadium oxide VO2. The anode layer 116 can be printed as a conductive zinc ink, or be provided as a zinc foil (116) PSA (260) laminate as shown in the figures, either of which can be made about 0.20" wide and about 0.002" (0.001"-0.010") thick. In various other examples, the anodes can be printed using an ink that includes one or more of zinc, nickel, cadmium, metal hydrides of the AB2 and the AB3 types, iron, and FeS2. Still, the anodes and/or cathodes can be provided via a non-printed process, such as laminates, adhesives, strips of material, etc. In an alternative example, the anodes can be provided as a zinc foil PSA laminate, either of which can be made with corresponding geometry to match the cell geometry and about 0.002" (0.001"-0.010") thick.

After the electrode layers (anode layer 116 and cathode layer 130) are in place, an optional "picture frame" 113 can be placed around the electrodes as a spacer. One method is to print this cell picture frame with a dielectric ink, for example, such as a cured or dried adhesive ink. Another method is to utilize a polymer sheet, stamped, die cut, laser cut or similar methods to form the appropriate "pockets" (inner space or spaces) to house materials of each unit cell. In the simplified construction being discussed here, the picture frame could comprise a die cut polymer laminate sheet, such as a polyester or polyvinyl chloride (PVC), etc., in the middle and having two outside layers of pressure sensitive adhesive with release liners (e.g., top surface and bottom surface). The top PSA layer adheres and seals the top laminate substrate to the picture frame and bottom PSA layer can be used to adhere and seal the bottom laminate substrate to the picture frame. Alternatively, the picture frame could be replaced by a printed or laminated adhesive provided in the shape of the above-described frame.

In the shown example, the optional picture frame 113 can comprise a die cut polymer laminate sheet, such as a polyester or polyvinyl chloride (PVC) etc., and can be further provided with two layers of pressure sensitive adhesive (118 on the top surface and 117 on the bottom surface). The top pressure sensitive adhesive (PSA) layer 118 seals the top laminate substrate 112 to the picture frame 113 and bottom PSA layer 117 can be used to seal the bottom laminate substrate 111 to the picture frame 113. Generally, when stamped frames are used, each "picture frame" has a total thickness (excluding the thickness of the liners) of about 0.010" (about 0.005"-0.50"). The "picture frame" can be placed on the bottom laminate structure after removing a bottom release liner so that the anode and cathode are centered within the frame. When a printed frame is used, they are generally much thinner with a thickness of about 0.002" (e.g., about 0.0005"-0.005"). In some cases, to ensure a leak-free construction, a sealing and/or caulking adhesive, a heat sensitive sealant, and/or double sided PSA tape can be placed and/or printed on top of the anode layer and on top of cathode collector in an area that falls under the picture frame. The sealing adhesive can also be provided underneath the remainder of the picture frame. In the shown example, the picture frame can be placed on the lower laminate substrate 111 after removing a bottom release liner so that the electrodes are centered within the frame. In some cases, to ensure a leak-free construction, a sealing and/or caulking adhesive, a heat sensitive sealant, and/or double sided PSA tape 253 can be placed and/or printed on top of the anode 116 and on top of cathode collector layer 131 in an area that falls under the picture frame 113. The sealing adhesive 253 can also be provided underneath the remainder of the optional picture frame 113. In the various shown examples the "picture frame" can have an exterior geometry that generally corresponds to the overall geometry of the battery, and an interior area that generally provides an inner space for each electrochemical cell.

The anodes and cathodes of the electrochemical cell interact through the electrolyte to create an electrical current. The electrolyte can include one or more of: zinc chloride, ammonium chloride, zinc acetate, zinc bromide, zinc Iodide, zinc tartrate, zinc per-chlorate, potassium hydroxide, and sodium hydroxide. The liquid electrolyte layer can comprise a polymeric thickener comprising one or more of polyvinyl alcohol, a starch, a modified starch, ethyl and hydroxyl-ethyl celluloses, methyl celluloses, polyethylene oxides, and polyacryamides. Additionally, the electrolyte layer can further comprise an absorbent paper separator. As described herein, the electrolyte is a viscous or gelled electrolyte. If the electrolyte is not part of the gelled coating, a cell electrolyte 120 is provided to an absorbent material such as a "paper separator" 126 (not shown in FIG. 5 for clarity, see FIG. 6) that covers or partially covers both electrodes. The electrolyte can be an aqueous solution of $ZnCl_2$ at weight percent of about 27% (about 23%-43%) that could also contain a thickener, such as carboxymethylcellulose (CMC) or other similar materials at about 0.6% level (about 0.1%-2%). Any of the electrolytes can include an additive to prevent or reduce gassing in the electrochemical cell (e.g., prevent or reduce the generation of hydrogen gas in the cells).

The cell is completed by applying and sealing the top laminate 112 over the picture frame using the PSA and/or with a heat seal. The top laminate substrate 112 is connected to the bottom laminate substrate 112 to contain the liquid electrolyte such that the electrochemical cell is sealed. If present, the top laminate substrate 112 can be sealed over the optional picture frame. Prior to applying the top laminate substrate 112, a release liner, if present (not shown), is removed from an adhesive layer on top of the optional picture frame. In another example, a printed adhesive can be used to connect the top and bottom laminate substrates 111, 112. Additionally, the printed adhesive may extend over and cover at least a portion of the anode and/or cathode layers. In another example, the top and bottom laminate substrates 111, 112 can be directly connected to each other without an intermediate adhesive or picture frame. It is also contemplated that where a picture frame is not utilized, the top laminate substrate 112 is connected to the bottom laminate substrate 111 to form an inner space containing the liquid electrolyte.

When the top laminate substrate 112 is sealed over the bottom laminate substrate 111, an outer seal area is formed. The seal area inhibits, such as prevents, the liquid electrode from leaking out of each cell. The width of the seal area can vary based on the overall size and geometry of the battery. In one example, the seal area can have a minimum width of about 0.075 inches. The maximum width can vary based on the various batteries, and can be as large as 0.250 inches, or even greater. This battery construction with the same geometries can also be made without the frame in high volumes with a commercial pouch filling machine. It is contemplated that the seal area may be substantially the same around the perimeter of each cell, or may differ along the perimeter of each cell as desired.

The batteries described herein have a co-planar construction. A co-planar construction provides several advantages, in that they are easy to manufacture, provide consistent, reliable performance, and have their contacts on the same side of the cell/battery. Generally, each of the electrochemical cells described herein can provide about 1.5 volts. However, a number of the electrochemical cells can be electrically coupled together if higher voltages and/or high capacities are desired. For example, a 3 volt battery is obtained by connecting two 1.5 volt unit cells in series, although other voltages and/or currents can be obtained by using unit cells with different voltages and/or by combining different numbers of cells together either in series and/or in parallel. Different electrochemical systems could be customized for the different battery configurations. Preferably, if different cells are used to obtain higher voltages all of the cells in each battery should be of the same electrochemical system. Thus, applications using greater voltages can connect unit cells in series, whereas applications requiring greater currents and/or capacities, unit cells can be connected in parallel, and applications using both can utilize various groups of cells connected in series further connected in parallel. Thus, a variety of applications that use different voltages and currents can be supported using a variety of unit cell and/or battery configuration.

Example manufacturing schemes for the battery will now be discussed. It can be beneficial to print the entire battery, including all cells, in a single printing process to avoid the difficulty of later connecting the multiple cells together. The printing process can be partially or completely automated, and may utilize individual sheets or a roll-to-roll process. The individual batteries can be removed from the carrier for use.

To make the manufacturing process of a cell/battery more efficient and/or achieve greater economies of scale, the cell/battery can be manufactured using a generally continuous web in a reel-to-reel printing process to provide production at high speeds and low cost. An example manufacturing procedure is described in the following paragraphs. In this example procedure, the cell/battery proceeds through numerous stations that are compatible with a high-speed printing press running a roll-to-roll setup. Though not further described herein, the processing and assembly could be integrated with the manufacture of the flexible battery or elements thereof to be powered by the battery, such as with the electrical component, etc.

According to available printing presses, the cells could be made with one pass, or multiple passes, on a given press, for example. As an example, two rows of individual cells on the web; however, the number of rows is limited only to the size of the unit cells and the maximum web width that the press can process. Because there may be numerous steps, thereby likely utilizing a long and complicated press, some of these steps, as well as some of the materials, could be modified and/or multiple passes of a press or multiple presses could be used. Some modified process summaries will be shown after the initial discussion is completed. Moreover, any or all of the printing steps can be performed by screen printing, such as by flat bed screens or even rotary screen stations. Additionally, one skilled in the art would realize that one printing press with more than five stations could be difficult to find and or to operate, and thus the following discussion of the process could occur on one or more presses or even multiple passes through one press.

During manufacturing, various optional operations may or may not occur. For example, the optional operations could include one or both of heat stabilization of the web and graphics printing (which could include logos, contact polarities, printing codes and the addition of registration marks on the outside surface of web). If these optional printing operations occur on the web, then the web can be turned over and the functional inks can be printed on the inside surface, (i.e., the heat seal layer).

One skilled in the art would realize that there are many methods, materials, and sequences of operations that could be used, and that more or less, similar or different, numbers of stations could also be utilized. Still, it is to be understood that the following process can also be utilized for the manufacture of various other integrated electrical devices. Further, for the purposes of clarity only one column of batteries will be described and illustrated with the understanding that such description can similarly apply to other columns. Moreover, it is to be understood that any or all of the following elements can include any of the various materials, chemical compositions, etc. described throughout this document. Additionally, the various steps are intended to be merely example steps, and it is to be understood that the steps can include various other steps, alternatives, etc. as discussed herein.

As discussed herein, any or all of the substrates can be provided as generally continuous webs that can be processed through a "reel-to-reel" style manufacturing process. For example, a first substrate can be provided as a generally continuous web from a source station, which can be a source roll or the like. Some or all of the various processing steps, such as, for example, the steps of providing said cathode and anode collectors, cathode layer, anode layer, contacts, optional frame, optional printed circuitry, etc., can then be performed by passing the generally continuous web through a printing station, or even multiple printing and/or converting stations. In addition or alternatively, the process can be adapted to pass the web through the printing station in multiple passes. Finally, the completed batteries on the generally continuous web can be collected at a take-up station, which can include a collection roll. Alternatively, the completed batteries can be provided on flat sheets with a plurality of batteries, such as 20 or more batteries per sheet.

The manufacturing process can include various other stages, steps, etc. For example, prior to or after the printing station, the web can pass through an auxiliary station wherein various electrical components could be provided. Moreover, any or all of the various layers, substrates, etc. can be provided by supplemental rolls along the process. For example, an additional substrate (i.e., a spacer layer) can be provided by a supplemental roll via a supplemental web. Though described as near the beginning of the printing station, it is to be understood that any or all of the supplemental webs can be provided at various locations along the manufacturing process. In addition or alternatively, waste material, such as release layers or the like, can be removed from as a waste web and taken-up by a waste roll or the like. Various other pre-processing and/or post-processing stations, steps, etc. can also be included. It is to be understood that the various stations, rolls, etc. of the described process can be utilized in various orders, and additional equipment may even be provided (e.g., idler rollers, tension rollers, turn-bars, slit or perforators, etc.) to facilitate a sheet-fed or reel-to-reel process.

Various other additional steps can be utilized to provide additional structure, features, etc. to the completed battery cells and electrical components. In one example, an outer portion of the device, such as either or both of the first or second substrates, can be provided with a method of attaching the battery cells to another object, surface, etc. As described herein, the battery 32 could be mechanically and electrically coupled to the circuit 34 by, such as via conductive pads between the battery electrodes 33A, 33B and the battery contact pads 35A, 35B. In other examples, the substrate(s) can include ultrasonic welding, a pressure sensitive adhesive, another adhesive layer, a hook-and-loop style fastener, a liquid or hot-melt adhesive, etc. In another example, an outer portion of the battery cells, such either or both of the first or second substrates, can be provided with printed indicia or even a label or the like.

Figure 9:
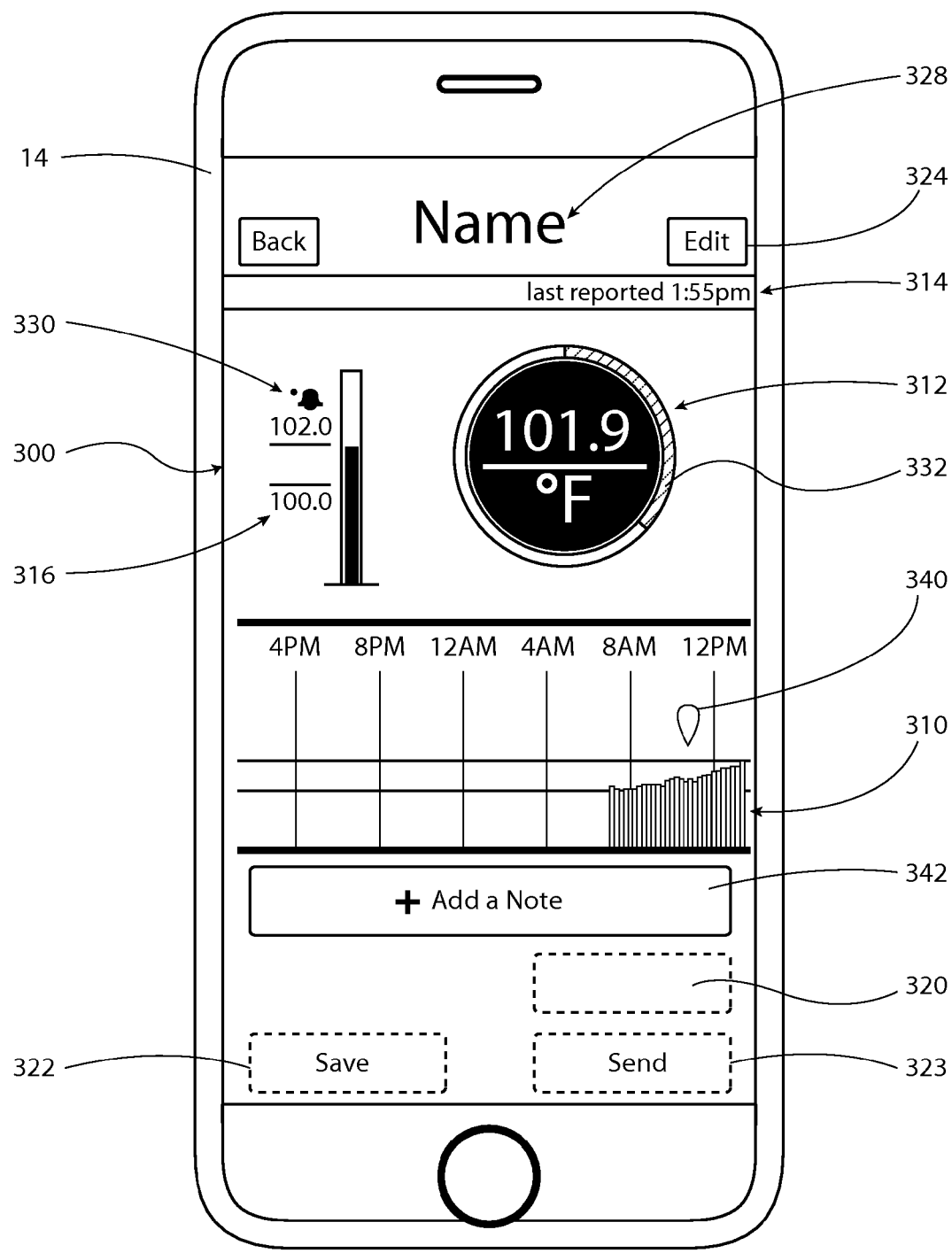
FIG. 9 illustrates an example screenshot of a user application for a smartphone or other computing device.

Turning now to FIG. 9, functionality of the software application will be described in greater detail. It is contemplated that the computing device 14 includes a microprocessor capable of running a software application configured to interface with the patch 10 via at least one-way communication (i.e., receive data communication from the patch 10), although could use two-way communication if enabled on the patch 10. The computing device 14 includes a display to graphically represent the temperature datapoints and other information to a user. As shown, one example visual display of the software application 300 is illustrated running on a display of the computing device 14. Although shown in a particular manner, it is understood that the graphic display of the software application 300 can appear variously in many configurations, as is known in the software fields.

In operation, the software application 300 can accept one or more initialization commands or conditions from the computing device 14 at the first time the patch 10 is used, including any or all of: high temperature boundary level; low temperature boundary level; interval of temperature reads; initialization of a time stamp to begin data logging; and optionally a flag that the electronics were successfully initiated. These initialization commands or conditions can be automatic, semi-automatic, or manual. In one example, a user can manually set a desired alert temperature, so that if the software application 300 receives a temperature reading at or above the selected alert temperature then the software application 300 provides a suitable alert to the user (visual, audible, tactile alerts). The software application 300 could also utilize global initialization commands or conditions for the above that are pre-set by a user and then subsequently applied by the software application 300 each time a patch 10 is activated and tracked. If two-way communication is enabled, the microprocessor of the patch 10 could be capable of transmitting a confirmation signal or flag back to the external computing device 14 that is indicative of a successful initiation. It is contemplated that if the electronics were not successfully initiated, the software application 300 can accept one or more re-initialization commands from the computing device 14 until the patch 10 is successfully initiated, or until the software application 300 determines that the patch 10 is faulty.

Generally, upon activation the software application 300 graphically displays the temperature history 310 of the patient over time, such as in a line chart, bar chart, etc. The graphical temperature history 310 can be scrollable and can allow dynamic zooming in/out capabilities to permit the user to better understand the sensed temperature changes over a desired time scale. The temperature data could also be presented in a scrollable tabular or chart format, and the user could toggle between the multiple views by on-screen buttons 320 or the like. It is also contemplated that as the user zooms in/out or scrolls across the temperature history 310 graph, the axes of the graph (x-axis time, y-axis temperature) could dynamically adjust to present a more relevant view of information to the user based upon the temperature datapoints shown in the particular zoomed or scrolled view. Additionally, because the patch 10 may be used for an extended period of time, the x-axis timeline could dynamically adjust between showing minutes or hours based upon the particular zoomed or scrolled view or overall elapsed time.

The software application 300 further displays the current temperature 312 of the patient based upon the most recent temperature datapoint obtained. Other temperature information could be provided, including preprogrammed and/or adjustable upper or lower temperature limits. For example, the upper or lower temperature limits can be graphically represented on the temperature history 310 chart for comparison with the sensed temperature trend over time, and/or could be used to set alarms to alert the user that the patient's temperature is approaching or has exceeded a particular threshold temperature. For example, such alarms could trigger a visual, audible, and/or tactile (e.g., vibration) alert from the computing device 14 to alert the user. In one example, the display of the current temperature 312 could change colors (e.g., green=ok, orange=caution, red=fever). In another example, a visual alert 330 (static or flashing) could be shown on the main display. In addition or alternatively, a gauge 332 could be provided about the current temperature 312 display that can progressively increase or decrease, and/or change color, depending upon how high or low the current temperature is. The gauge 332 could operate in an absolute manner, in a pre-programmed manner, or even in a relative manner if a user-set maximum or alert temperature is input into the software application 300. Alternatively, the visual alert could be shown in a status location of the computing device 14, such as along the top of the graphical display. Thus, even if a user is not actively viewing the software application 300, it could still be operating in the background (possibly still collecting temperature data) and issuing an alert 330, if appropriate.

The software application 300 can also display time data 314, such as any or all of the time the patch 10 was activated, the time the patch 10 was deactivated or stopped transmitting, a delay time therebetween, and/or the last time communication occurred with the patch 10. In addition or alternatively, the time data 314 could also display an actual or estimated amount of operational time left for the patch 10 before the available battery power is depleted. The amount of operational time left for the patch 10 could be an actual amount of time, based upon a sensed voltage or the like of the battery that is transmitted by the patch 10, which can be correlated with a known power draw rate of the battery based upon initial voltage, battery capacity, the temperature-read interval, the communication interval, etc. Alternatively, amount of operational time left for the patch 10 could be an estimated time, based upon a known start time for the patch 10 and a known expected operational time (e.g., 12, 16, or 24 hours). The estimated operational time could be adjusted by the software application 300 based upon predetermined knowledge of the battery, and/or even by certain dynamic variables, such as the temperature-read interval, the communication interval, etc.

The software application 300 can further display auxiliary information 316 related to the status of the patch 10, such as any or all of an average temperature detected, a maximum temperature detected, a minimum temperature detected, the number of temperature datapoints acquired, etc. Any or all of this data could be visible to the end user, or could be selectively hidden. It is contemplated that any or all of the average, maximum, and minimum temperatures could be based upon a portion, such as some or all of the collected temperature datapoints. In one example, any or all of the average, maximum, and minimum temperatures could be dynamically shown based user-selected data, such as upon a zoomed-in/out or scrolled view shown in the temperature history 310 or associated tabular data. Temperature triggers could also be pre-programmed or even user programmable, such as temperatures to indicate an elevated temperature (e.g., 100 degrees F.) or a fever temperature (e.g., 102 degrees F.). A graphical representation of the maximum temperature detected, minimum temperature detected, and/or other desired values can be shown. In addition or alternatively, the software application 300 can include optional features 324 to adjust the display of the data, such a temperature unit switch that can dynamically adjust and display the temperature datapoints in either Fahrenheit or Celsius units (or other temperature units, as desired).

The software application 300 can further provide the ability to annotate the temperature history 310 chart with one or more notes. For example, the software application 300 can provide an annotation 340 upon the temperature history 310 chart that is displayed at a particular time and/or temperature reading. In the shown example, the annotation 340 is displayed at the time of about 11 AM. The annotation 340 can be provided as an automatic, semi-automatic, or manual feature. The software application 300 can provide an "Add a Note" button 342 that enables a user to manually annotate the chart with automatic and/or user-supplied information. The annotation 340 can be useful to remind the user of particular events, such as a time when medication was administered to the patch wearer, or when the patch wearer went to sleep, etc. The note can then help the user to understand the effects or results of the patch wearer, such as if a medication helped to subsequently reduce the patch wearer's temperature. In the shown example, the user can press the "Add a Note" button 342, which will display the annotation 340 upon the temperature history 310 chart at that particular time. The software application 300 can then present the user with a text-input box that can enable the entry of a manual note. Thereafter, the annotation 340 can be selected by the user and will display the note. Multiple notes can be entered by the user, and each can display an annotation 340 along the temperature history chart 310. It is contemplated that additional features can be provided. For example, the "Add a Note" button 342 could automatically add data to the note's text information, such as any of the time, temperature, patch wearer name, date, max/min temperature, etc. The software application 300 could also provide the ability to add notes at a later time (i.e., a back-date feature). By default, the "Add a Note" button 342 can display the annotation 340 at that particular time, but the user could change the time to a previous time and the annotation 340 could then display the appropriate temperature recorded at the newly-chosen time, and allow the user to add a manual note. Finally, it is contemplated that the software application 300 will allow the user to save the temperature history 310 chart for later reference, together with all of the added annotations 340. Thus, if a parent has a child that uses a number of patches 10 at different times (i.e., each time the child is sick), then the parent can recall previous temperature history 310 charts saved to that child's profile to compare a previous temperature-history profile against a current temperature history chart, or compare the historical effects of medication on the child's temperature, etc. Indeed, the software application 300 could even graphically overlay two or more temperature history charts for a graphical comparison.

The software application 300 can also include other additional features. In one example, a unique identification (UID) 328 of the patch 10 can be displayed. The UID 328 could be displayed in real-text, or an easier to understand alias (e.g., the patient's name or hospital code) could be assigned to the UID of the patch 10. The user could also toggle between the UID 328 and alias as desired, or this feature could even be limited or protected to provide anonymity to the patient. Finally, the software application 300 could provide the ability to save and/or transmit the collected temperature data. For example, a Save button 322 could be provided to save a partial or complete set of the collected datapoints (temperature and/or time), temperature history 310 charts, annotations 340, etc. in local or remote computer storage memory for later review. It is contemplated that a repeat user could setup a user profile (e.g., one profile for each child in a family) and save that user's data to that particular user profile each time a new patch 10 is used. In addition or alternatively, a Send button 323 could be provided to transmit a partial or complete set of the collected datapoints to a remote party, such as to a doctor, hospital, or other individual. It is contemplated that the data saved and/or sent could include some or all of the temperature datapoints, temperature history 310 charts, annotations 340, time information, UID information, etc. The software application 300 could further provide for patient profiles for patients that often use multiple patches 10 over time, such as a child that might use a patch 10 each time they are sick. Thus, the parent or doctor could recall historical temperature information for that particular child to enable comparison and diagnosis. It is further contemplated that the data saved and/or sent could be locally or remotely encrypted or even made anonymous. In yet another feature, the software application 300 could provide a programmable or pre-determined reminder to take certain actions for the user or patient, such as replacing the patch 10, syncing with the patch 10, taking medication, transmitting data to a doctor, scheduling a doctor's visit, etc.

In addition or alternatively, various security and/or privacy layers can be provided to either or both of the patch 10 and the computing device 14. For example, the wireless data transmitted and received can be encrypted via hardware and/or software mechanisms locally on the patch and/or at the computing device 14. Either or both of the patch and the computing device 14 can utilize user ID and password(s). The wireless data transmission and/or reception can be limited to authorized paired devices, and/or the wireless data transmission range can be artificially restricted to a predetermined distance. For example, when using the Bluetooth protocol, each patch 10 can be set to pair with the computing device 14 by a predetermined passcode, such as a four-digit passcode. Thus, to pair the patch 10 with the computing device, the user could be required to enter the correct four-digit passcode associated with the patch. A default passcode could be used with all patches 10, such as "0000" or the like. Alternatively, each patch 10 could be pre-programmed with a unique passcode, which is provided together with the patch (e.g., printed on, provided on a separate insert, etc.) Thus, only the user of the patch that knows the unique passcode of a particular patch can pair it with the computing device to receive the data transmitted by that patch 10. The software application 300 could utilize a passcode or password to enable activation of the app, or could even require a passcode or password on a per user profile basis. Alternatively, the security protocols of Bluetooth or NFC could be used to secure and bootstrap other wireless connections. The patch could include a hardware and/or software switch to disable or otherwise restrict wireless data transmission and/or reception. In one example, a hardware switch (e.g., such as switch 46) could completely disable the patch. In another example, a time-lock could restrict wireless data transmission and/or reception during particular times or time intervals. Data read from the patch may be automatically deleted or maintained in the memory of the software application and/or patch 10. Any or all of the foregoing security and/or privacy layers can be used together, and additional layers can also be used.

The invention has been described hereinabove using specific examples and embodiments; however, it will be understood by those skilled in the art that various alternatives may be used and equivalents may be substituted for elements and/or steps described herein, without deviating from the scope of the invention. Modifications may be performed to adapt the invention to a particular situation or to particular needs without departing from the scope of the invention. It is intended that the invention not be limited to the particular implementations and embodiments described herein, but that the claims be given their broadest interpretation to cover all embodiments, literal or equivalent, disclosed or not, covered thereby.

What is claimed is:

1. An actively-powered temperature data logger patch with wireless data communication, comprising:
  a first substrate layer comprising a first end and an opposite second end;
  a plurality of sealed, flexible batteries in a parallel arrangement and configured to provide continuous electrical power, each battery comprising a printed electrochemical cell with an anode and a cathode that are provided in a co-planar arrangement and an aqueous electrolyte layer covering and in electrical contact with said anode and cathode;
  a flexible circuit comprising a microprocessor, a temperature sensor configured to sense a temperature of a target subject, a wireless communication transmitter and an antenna, the flexible circuit further comprising a plurality of contact pads that are electrically coupled to corresponding contacts of the plurality of flexible batteries to thereby electrically power the microprocessor, wireless communication transmitter, and temperature sensor,
  wherein all of the microprocessor, temperature sensor, and wireless communication transmitter actively receive electrical power from the flexible batteries to enable the microprocessor to continuously obtain a plurality of temperature samples from the temperature sensor at a periodic time interval;
  a second substrate layer comprising an adhesive configured to be removably applied to a surface of the target subject,
  wherein the flexible batteries and flexible circuit are disposed between the first and second substrate layers, and all of the first substrate layer, flexible batteries, flexible circuit, and second substrate layer are sufficiently flexible so that the temperature data logger patch is configured to conform to a curved or variable surface of the target subject and is able to flex and move together with movement of the target subject without degradation of the batteries, circuit, or active operation thereof; and
  a switch used to activate the microprocessor to an operational power state and thereby enable said active electrical power to the microprocessor, temperature sensor, and wireless communication transmitter only when a user intends to begin use of the patch.

2. The patch of claim 1, further comprising a latching power circuit in electrical communication with the switch and the microprocessor, and upon actuation of the switch the latching power circuit enables electrical communication between the plurality of sealed, flexible batteries and the microprocessor to thereby activate the microprocessor from a reduced power state to the operational power state.

3. The patch of claim 1, wherein the switch is a momentary switch.

4. The patch of claim 1, wherein the microprocessor is configured to selectively provide electrical power to the temperature sensor only when the microprocessor is obtaining a temperature sample from the temperature sensor.

5. The patch of claim 1, wherein the wireless communication transmitter utilizes a standard Bluetooth or Bluetooth low-energy communications protocol.

6. The patch of claim 1, wherein the microprocessor further comprises a timer that actively receives electrical power from the flexible batteries and is configured to enable the microprocessor to obtain temperature samples from the temperature sensor at the periodic time interval, and the microprocessor further comprises a non-transitory memory for storing the temperature samples together with an associated numerical identifier for each temperature sample.

* * * * *